(12) United States Patent
Low et al.

(10) Patent No.: US 8,586,595 B2
(45) Date of Patent: Nov. 19, 2013

(54) POSITRON EMISSION TOMOGRAPHY IMAGING METHOD

(75) Inventors: Philip Stewart Low, West Lafayette, IN (US); Sumith K. Kularatne, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 299 days.

(21) Appl. No.: 12/526,096

(22) PCT Filed: Feb. 7, 2008

(86) PCT No.: PCT/US2008/053293
§ 371 (c)(1),
(2), (4) Date: Aug. 6, 2009

(87) PCT Pub. No.: WO2008/098112
PCT Pub. Date: Aug. 14, 2008

(65) Prior Publication Data
US 2010/0322854 A1    Dec. 23, 2010

Related U.S. Application Data

(60) Provisional application No. 60/899,921, filed on Feb. 7, 2007, provisional application No. 60/896,018, filed on Mar. 21, 2007.

(51) Int. Cl.
*A01N 43/90* (2006.01)
*A61K 31/519* (2006.01)
*C07D 475/00* (2006.01)

(52) U.S. Cl.
USPC ....................................... 514/262.1; 544/258

(58) Field of Classification Search
None
See application file for complete search history.

(56) References Cited

U.S. PATENT DOCUMENTS

| | | |
|---|---|---|
| 2,816,110 A | 12/1957 | Sletzinger et al. |
| 4,577,636 A | 3/1986 | Spears |
| 4,641,650 A | 2/1987 | Mok |
| 4,713,249 A | 12/1987 | Schroder |
| 4,718,417 A | 1/1988 | Kittrell et al. |
| 4,785,806 A | 11/1988 | Deckelbaum |
| 4,817,601 A | 4/1989 | Roth et al. |
| 4,850,351 A | 7/1989 | Herman et al. |
| 4,917,084 A | 4/1990 | Sinofsky |
| 4,950,266 A | 8/1990 | Sinofsky |
| 5,094,848 A | 3/1992 | Brixner |
| 5,108,921 A | 4/1992 | Low et al. |
| 5,140,104 A | 8/1992 | Coughlin et al. |
| 5,192,525 A | 3/1993 | Yang et al. |
| 5,217,456 A | 6/1993 | Narciso |
| 5,266,333 A | 11/1993 | Cady et al. |
| 5,275,594 A | 1/1994 | Baker et al. |
| 5,336,506 A | 8/1994 | Josephson et al. |
| 5,373,093 A | 12/1994 | Vallarino et al. |
| 5,399,338 A | 3/1995 | Born et al. |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,562,100 A | 10/1996 | Kittrell et al. |
| 5,576,305 A | 11/1996 | Ratcliffe |
| 5,688,488 A | 11/1997 | Low et al. |
| 5,753,631 A | 5/1998 | Paulson et al. |
| 5,759,546 A | 6/1998 | Weinberg et al. |
| 5,820,847 A | 10/1998 | Low et al. |
| 6,093,382 A | 7/2000 | Wedeking et al. |
| 6,167,297 A | 12/2000 | Benaron |
| 6,204,371 B1 | 3/2001 | Levinson |
| 6,217,847 B1 | 4/2001 | Contag et al. |
| 6,221,334 B1 | 4/2001 | Wedeking et al. |
| 6,246,901 B1 | 6/2001 | Benaron |
| 6,270,766 B1 | 8/2001 | Feldman et al. |
| 6,335,434 B1 | 1/2002 | Guzaev et al. |
| 6,365,362 B1 | 4/2002 | Terstappen et al. |
| 6,387,350 B2 | 5/2002 | Goldenberg |
| 6,507,747 B1 | 1/2003 | Gowda et al. |
| 6,780,984 B2 | 8/2004 | Wang et al. |
| 6,782,289 B1 | 8/2004 | Strauss |
| 6,960,449 B2 | 11/2005 | Wang et al. |
| 7,033,594 B2 | 4/2006 | Low et al. |

(Continued)

FOREIGN PATENT DOCUMENTS

| | | |
|---|---|---|
| EP | 1940473 | 7/2008 |
| JP | 2003-534388 | 11/2003 |

(Continued)

OTHER PUBLICATIONS

Beaumont, Andrew J., et al., "Selective Fluorodenitration of Chloronitroaromatics", 1993, *J. Fluorine Chem.*, vol. 63, pp. 25-30.
Boechat, Nubia, et al., "Fluorodenitrations Using Tetramethylammonium Fluoride", 1993, *J. Soc., Chem. Commun.*, pp. 921-922.
Cox, D. Philip, et al., "Anhydrous, Tetrabutylammonium Fluoride: A Mild but Highly Efficient Source of Nucleophilic Fluoride Ion", 1984, *J. Org. Chem.*, No. 49, pp. 3216-3219.

(Continued)

*Primary Examiner* — Jeffrey Murray
(74) *Attorney, Agent, or Firm* — Barnes & Thornburg LLP

(57) ABSTRACT

Described herein are compositions and methods for diagnosing and/or monitoring pathogenic disease states using positron emission tomography, wherein the pathogenic cells uniquely express, preferentially express, or overexpress vitamin receptors. Also described herein are $^{18}F$ conjugates of vitamins and vitamin receptor-binding analogs of the formula.

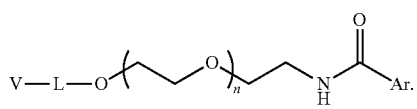

13 Claims, 1 Drawing Sheet

(56) References Cited

U.S. PATENT DOCUMENTS

| | | | |
|---|---|---|---|
| 7,128,893 | B2 | 10/2006 | Leamon et al. |
| 7,223,380 | B2 | 5/2007 | Yang et al. |
| 7,381,535 | B2 | 6/2008 | Perez et al. |
| 7,601,332 | B2 * | 10/2009 | Vlahov et al. ............ 424/1.73 |
| 2001/0031252 | A1 | 10/2001 | Low et al. |
| 2002/0127181 | A1 | 9/2002 | Edwards et al. |
| 2002/0192157 | A1 | 12/2002 | Low et al. |
| 2003/0162234 | A1 | 8/2003 | Jallad et al. |
| 2003/0198643 | A1 | 10/2003 | Lu |
| 2003/0219375 | A1 | 11/2003 | Piwnica-Worms |
| 2004/0033195 | A1 | 2/2004 | Leamon et al. |
| 2004/0057900 | A1 | 3/2004 | Edwards et al. |
| 2004/0136910 | A1 | 7/2004 | Jallad et al. |
| 2004/0184990 | A1 | 9/2004 | Larsen et al. |
| 2004/0242582 | A1 | 12/2004 | Green et al. |
| 2005/0002942 | A1 | 1/2005 | Viahov et al. |
| 2005/0026866 | A1 | 2/2005 | Pawelek |
| 2005/0227985 | A9 | 10/2005 | Green et al. |
| 2005/0244336 | A1 | 11/2005 | Low |
| 2006/0002891 | A1 | 1/2006 | Pouletty |
| 2006/0067946 | A1 | 3/2006 | Low et al. |
| 2006/0134002 | A1 | 6/2006 | Lin |
| 2006/0182687 | A1 | 8/2006 | Yang et al. |
| 2006/0204565 | A1 | 9/2006 | Low et al. |
| 2007/0009434 | A1 | 1/2007 | Low et al. |
| 2007/0031334 | A1 | 2/2007 | Leamon et al. |
| 2007/0231266 | A1 | 10/2007 | Low et al. |
| 2007/0276231 | A1 | 11/2007 | Low et al. |
| 2008/0119475 | A1 | 5/2008 | Low et al. |
| 2008/0138396 | A1 | 6/2008 | Low et al. |
| 2008/0254499 | A1 | 10/2008 | Low et al. |
| 2009/0012009 | A1 | 1/2009 | Low et al. |
| 2010/0055735 | A1 | 3/2010 | Low et al. |
| 2010/0322854 | A1 | 12/2010 | Low et al. |

FOREIGN PATENT DOCUMENTS

| | | |
|---|---|---|
| RU | 21 23338 | 11/1996 |
| WO | 90/01296 | 10/1990 |
| WO | 91/19501 | 12/1991 |
| WO | 91/19502 | 12/1991 |
| WO | 96/22521 | 7/1996 |
| WO | 96/36367 | 11/1996 |
| WO | 97/37690 | 10/1997 |
| WO | 01/19320 | 3/2001 |
| WO | 01/39806 | 6/2001 |
| WO | 01/47552 | 7/2001 |
| WO | 01/74382 | 10/2001 |
| WO | WO 01/91807 | 12/2001 |
| WO | 02/087424 | 11/2002 |
| WO | WO 2004/044227 | 5/2004 |
| WO | 2004/069159 | 8/2004 |
| WO | WO2004/110250 A | 12/2004 |
| WO | WO 2005 049579 | 6/2005 |
| WO | WO 2005 067644 | 7/2005 |
| WO | 2005/087275 | 9/2005 |
| WO | 2006/012527 | 2/2006 |
| WO | 2006/034046 | 3/2006 |
| WO | 2006/065943 | 6/2006 |
| WO | WO2006/071754 A | 7/2006 |
| WO | WO2006/101845 A | 9/2006 |
| WO | 2007/006041 | 1/2007 |
| WO | WO 2007 001466 | 1/2007 |
| WO | WO 2007/038346 | 4/2007 |
| WO | 2008/148001 | 4/2008 |
| WO | 2008/057437 | 5/2008 |
| WO | 2008/098112 | 8/2008 |
| WO | WO2009/002993 A | 12/2008 |
| WO | 2009/026177 | 2/2009 |

OTHER PUBLICATIONS

Johnström, Peter, et al.,
Garg, Pradeep K., et al., "Fluorine-18 Labeling of Monoclonal Antibodies and Fragments with Preservation of Immunoreactivity", 1991, Bioconjugate Chem., vol. 2, No. 1, pp. 44-49.

Giroldo, Tatiana, et al, "An Unusually Fast Nucleophilic Aromatic Displacement Reaction: The Gas-Phase Reaction of Fluoride Ions with Nitrobenzene", 2004, Angew. Chem. Int. Ed., No. 43, pp. 3588-3590.

Hamacher, K., et al., "No-Carrier-Added Nucleophilic $^{18}$F-Lavelling in an Electrochemical Cell Exemplified by the Routine Production of [$^{18}$F]altanserin", 2006, Applied Radiation and Isotopes, No. 64, pp. 989-994. "$^{18}$F-Endothelin-1, a Positron Emission Tomography (PET) Radioligand for the Endothelin Receptor System: Radiosynthesis and In Vivo Imaging Using MicroPET", 2002, Clinical Science, vol. 103, Suppl. 48, pp. 45-85.

Leamon, Christopher, P., et al., "Synthesis and Biological Evaluation of EC140: A Novel Folate-Targeted Cinca Alkaloid Conjugate", 2006, Bioconjugate Chem., vol. 17, No. 5, pp. 1226-1232.

Lemaire, Christian, et al., "Fluorine-18-Altanserin: A Radioligand for the Study of Serotonin Receptors with PET: Radiolabeling and In Vivo Biologic Behavior in Rats", Dec. 1991, The Journal of Nuclear Medicine, vol. 32, No. 12, pp. 2266-2272.

Liotta, Charles L., et al., "The Chemistry of "Naked" Anions. I. Reactions of the 18-Crown-6 Complex of Potassium Fluoride with Organic Substrates in Aprotic Organic Solvents", Apr. 3, 1974, Journal of the American Chemical Society, vol. 96, No. 7, pp. 2250-2252.

Murakami, Yoshihiro, et al., "$^{18}$F-Labelled Annexin V: A PET Tracer for Apoptosis Imaging", Apr. 2004, European Journal of Nuclear Medicine and Molecular Imaging, vol. 31, No. 4, pp. 469-474.

Olma, Sebastian, et al., "4-[$^{18}$F]fluorophenyl ureas via carbamate-4-nitrophenyl esters and 4-[$^{18}$F]Fluoroaniline", 2006, Journal of Labeled Compd. and Radiopharm, vol. 49, pp. 1037-1050.

Sun, Haoran, et al., "Anhydrous Tetrabutylammonium Fluoride", 2005, J. Am. Chem. Soc., vol. 127, No. 7, pp. 2050-2051.

Sun, Haoran, et al., "Room-Temperature Nucleophilic Aromatic Fluorination: Experimental and Theoretical Studies", 2006, Angew. Chem. Mt. Ed., No. 45, pp. 2720-2725.

Sutcliffe-Goulden, Julie L., et al., "Solid Phase Synthesis of [$^{18}$F]Labelled Peptides for Positron Emission Tomography", 2000, Bio. & Medicin. Chem. Letters, No. 10, pp. 1501-1503.

Tan, Ping-Zhong, et al., "A Complete Remote-Control System for Reliable Preparation of [$^{18}$F]altanserin", 1999, Applied Radiation and Isotopes, vol. 50, pp. 923-927.

Westerhof, G. Robbin, et al., "Carrier-and Receptor-Mediated Transport of Folate Antagonists Targeting Folate-Dependent Enzymes: Correlates of Molecular-Structure and Biological Activity", 1995, Molecular Pharmacology, No. 48, pp. 459-471.

Achilefu et al., "Novel Receptor-Targeted Fluorescent Contrast Agents for In Vivo Tumor Imaging", Investigative Radiology, vol. 35, No. 8, pp. 479-485, Aug. 2000.

Antohe et al., "Increased uptake of folate conjugates by activated macrophages in experimental hyperlipemia", Cell Tissue Research, vol. 320, No. 2, pp. 277-285, May 2005.

Aviram et al., "Intralipid infusion abolishes ability of human serum to cholesterol-load cultured macrophages", Arteriosclerosis, vol. 9, pp. 67-75, 1989.

Ballou et al., "Tumor labeling in vivo using cyanine-conjugated monoclonal antibodies", Cancer Immunol Immunother, vol. 41, pp. 257-263, 1995.

Barrera et al., "Synovial macrophage depletion with clodronate-containing liposomes in rheumatoid arthritis", Arthritis and Reheumatism, vol. 43, pp. 1951-1959, Sep. 2000.

Becker et al., "Macromolecular Contrast Agents for Optical Imaging of Tumors: Comparison of Indotricarbocyanine-labeled Human Serum Albumin and Transferrin", Photochemistry and Photobiology, vol. 72, No. 2, pp. 234-241, May 14, 2000.

Bock et al., "Sulfonamide Structure-Activity Relationships in a Cell-Free System. 2. Proof for the Formation of a Sulfonamide-Containing Folate Analog", Journal of Medicinal Chemistry, 1974, vol. 17, No. 1, pp. 23-28, 1974.

Boente et al., "Screening, imaging, and Early Diagnosis of Ovarian Cancer", Clinical Obstetrics and Gynecology, vol. 37, No. 2, pp. 377-391, Jun. 1994.

Bonasera et al., "The Synthesis of [26, 27-11C]Dihydroxyvitamin D3, a Tracer for Positron Emission Tomography (PET), Bioorganic & Medicinal Chemistry", Elsevier Science Ltd., vol. 9, pp. 3123-3128, 2001.

(56) References Cited

OTHER PUBLICATIONS

Budinger et al., "New Approaches to Targeting Arthritis with Radiopharmaceuticals", The Journal of Rheumatology, 1995, 22(1) Supp: 62-67, 1995.
Burke et al., "Book Review. The Macrophage", British Journal of Cancer, vol. 89, p. 421, 2003.
Campbell et al., "Folate-binding Protein is a Marker for Ovarian Cancer", Cancer Research, vol. 51, pp. 5329-5338, Oct. 1, 1991.
Canis et al., "Lapascopic Diagnosis of Adnexal Cystic Masses: A 12-Year Experience With Long-Term Follow-Up", Obstetrics & Gynecology, vol. 83, No. 5, pp. 707-712, May 1994.
Case, "Ultrasound Physics and Instrumentation", Surgical Clinics of North America, vol. 78, No. 2, pp. 197-217, Apr. 1998.
Tung et al., "Preparation of a Cathepsin D Sensitive Near-Infrared Fluorescence Probe for Imaging", American Chemical Society, vol. 10, No. 5, pp. 692-696, Sep. 20, 1999.
Cochlovious, "Therapeutic Antibodies", Modern Drug Discovery, pp. 33-38, 2003.
Cohen et al., "Screening for ovarian cancer: The role of noninvasive imaging techniques", Am J. Obstet Gynecol., vol. 170, No. 4, pp. 1088-1094, 1994.
Cohen et al., "Three-Dimensional Power Doppler Ultrasound Improves the Diagnostic Accuracy for Ovarian Cancer Prediction", Gynecologic Oncology, vol. 82, pp. 40-48, 2001.
Degrado et al., "Synthesis and Evaluation of (18)F-Labeled Choline Analogs as Oncologic PET Tracers", J. Nuclear Medicine, vol. 42, No. 12, pp. 1805-1814, 2001.
DePriest et al., "Transvaginal Sonography as a Screening Method for the Detection of Early Ovarian Cancer", Gynecologic Oncology, vol. 65, No. GO974705, pp. 408-414, 1997.
Feldman et al., "Anti-TNFa Therapy Is Useful in Rheumatoid Arthritis and Crohn's Disease: Analysis of the Mechanism of Action Predicts Utility in Other Diseases", Transplant. Proc. , 30, pp. 4126-4127, 1998.
Forstner et al., "CT and MRI of ovarian cancer", Abdominal Imaging, vol. 20, pp. 2-8, 1995.
Godwin et al., "The synthesis of biologically active pteroyloligo-g-L-glutamates (folic acid conjugates): Evaluation of (3H) pteroylheptaglutamate for metabolic studies", Journal of Biological Chemistry. vol. 247, pp. 2266-2271, 1972.
Gotoh, "Causes and treatment of rheumatoid arthritis; recent trend I. Progress in pathogenesis of rheumatoid arthritis; role of macrophages and dendritic cells", Pharma Nedica, Japan Medical Review Co., Ltd., Tokyo, 1999, 17(10): 35-39, 1999.
Greenman et al., "Heterogeneous Expression of Two Somatostatin Receptor Subtypes in Pituitary Tumors," Journal of Clinical Endocrinology and Metabolism, vol. 78, No. 2, pp. 398-403, 1994.
Harris et al., "Human leukemic models of myelomonocytic development: a review of the HL-60 and U937 cell lines", Journal of Leukocyte Biology, vol. 37, No. 4, pp. 407-422, 1985.
Holmgren et al. "Strategies for the Induction of Immune Responses At Mucosal Surfaces Making Use of Cholera Toxin B Subunit As Immunogen, Carrier, and Adjuvan"t, Am. J. Trop Med Hyd, 50, pp. 42-54, 1994.
Hynes et al., "Quinazolines as Inhibitors of Dihydrofolate Reductase. 4. Classical Analogues of Folic and Isofolic Acids", Journal of Medicinal Chemistry, vol. 20, No. 4, pp. 588-591, 1977.
Jager et al., "Resection guided by antibodies (REGAJ): a diagnostic procedure during second-look operation in ovarian cancer patients", Depts of Obstetrics, Gynecology and Nuclear Medicine, Univ of Erlangen-Nurnberg, pp. 18-20, 1990.
Karlan, "The Status of Ultrasound and Color Doppler Imaging for the Early Detection of Ovarian Cancer", Cancer Investigation, vol. 15, No. 3, pp. 265-269, 1997.
Karlan et al., "Ovarian Cancer Screening: The Role of Ultrasound in Early Detection", Cancer Supplement, vol. 76, No. 10, pp. 2011-2015, Nov. 15, 1995.
Karsten et al., "Towards Usage-Based Accounting: Applying Policy-Based Intelligent Agents, ITC 15" Elsevier Science B.V., pp. 633-642, 1997.

Kennedy et al., "Evaluation of Folate Conjugate Uptake and Transport by the Choroid Plexus of Mice", Pharmaceutical Research, vol. 20, No. 5, p. 714-719, May 2003.
Kennedy et al., "Optical imaging of metastatic tumors using a folate-targeted fluorescent probe", J. of Biomedical Optics, vol. 8, No. 4, pp. 636-641, Oct. 2003.
U.S. Appl. No. 61/235,220, filed Aug. 19, 2009, Low et al.
U.S. Appl. No. 61/157,847, filed Mar. 5, 2009, Low et al.
Kim et al., "Synthesis and Biological Activity of 10-Thia-10-deaza Analogs of Folic Acid, Pteroic Acid, and Related Compounds", Journal of Medicinal Chemistry, vol. 18, No. 8, pp. 776-780, 1975.
Kinne et al., "Macrophage in rheumatoid arthritis", Arthritis Research, vol. 2, No. 3, pp. 189-202, 2000.
Konda et al., "Development of a Tumor-Targeting MR Contrast Agent Using the High-Affinity Folate Receptor", Investigative Radiology, vol. 35, No. 1, pp. 50-57, 2000.
Kramer, "Basic Principles of Magnetic Resonance Imaging", Radiological Clinics of North America, vol. 22, No. 4, pp. 765-778, Dec. 1984.
Kuriowa et al., "Development of a Fluorescein Operative Microscope for Use During Malignant Glioma Surgery", Elsevier Science Inc., vol. 50, pp. 41-49, 1998.
Leamon et al., "Folate-mediated targeting: from diagnosis to drug and gene therapy" DDT vol. 6 No. 1 44-51, Jan. 2001.
Leamon et al., "Synthesis and Biologicial Evaluation of EC20: A New Folate-Derived, 99mTc-Based Radiopharmaceutical" Bioconjugate Chemistry, vol. 13, No. 6, pp. 1200-1210, 2002.
Leamon et al., "Selective Targeting of Malignant Cells with Cytotoxin-Folate Conjugates", J. Drug Targeting 2: 101-112, 1994.
Lee et al., "Folic Acid Antagonists. Methotrexate Analogs Containing Spurious Amino Acids. Dichlorohomofolic Acid" Journal of Medicinal Chemistry, vol. 17, No. 3, pp. 326-330, 1974.
Licha et al., "Hydrophilic Cyanine Dyes as Contrast Agents for Near-infrared Tumor Imaging: Synthesis, Photophysical Properties and Spectroscopic In vivo Characterization, Photochemistry and Photobiology", vol. 72, No. 3, pp. 392-398, 2000.
Liu-Wu et al., "Identification and Analysis of Macrophage-Derived Foam Cells from Human Atherosclerotic Lesions by Using a 'Mock' FL3 Channel in Flow Cytometry", Cytometry, vol. 29, No. 2, pp. 155-164, 1997.
Low et al., "Ovarian Cancer: Comparison of findings with Perfluorocarbon-enhanced MR Imaging, In-111-CYT-103 Immunoscintigraphy, and CT", Depts of Diagnostic Rad and Onc, Sharp Memorial Hospital, vol. 195, No. 2, pp. 391-400, 1995.
Lu et al., "Folate-Targeted Enzyme Prodrug Cancer Therapy Utilizing Penicillin-V Amidase and a Doxorubicin Prodrug" J. Drug Targeting 7:43-53, 1999.
Mahmood et al., "Near Infrared Optical Imaging for Protease Activity for Tumor Detection", Radiology, 213:866-870, 1999.
Maiman et al., "Laproscopic Excision of Ovarian Neoplasm Subsequently Found to Be Malignant", Obstetrics & Gynecology, vol. 77, No. 4, pp. 563-565, Apr. 1991.
Mancini et al., "Relative contributions of apolipoprotein A and apolipoprotein B to the development of fatty lesions in the proximal aorta of mice", Arterioscler. Thromb. Vasc. Biol., vol. 15, pp. 1911-1916, 1995.
Mantovani et al., "Folate Binding Protein Distribution in Normal Tissues and Biological Fluids From Ovarian Carcinoma Patients as Detected by the Monoclonal Antibodies Mov 18 and Mov 19", European Journal of Cancer, vol. 30A, No. 3, pp. 363-369, 1994.
Mathias et al.,"Preparation of 66Ga- and 68GA-labeled GA(III)-deferoxamine-folate as potential folate-receptor-targeted PET radiopharmaceuticals", Nuclear Medicine and Biology, vol. 30, pp. 725-731, 2003.
U.S. Appl. No. 12/526,096, filed Aug. 6, 2009, Low et al.
Matsuyama et al., Clinical significance of the folate receptor beta expression in rheumatoid synovial macrophages, Rheumatoid, Japan College of Rheumatology, 41(2): 265, 2001.
Matsuyama et al., "Activation and pathological significance of macrophages in rheumatoid synovitis" Clinical Immunity, Japan, Kagaku Hyoronsha, Tokyo, 30(2): 214-219, 1998.
Mestas et al., Of Mice and Not Men: Differences between Mouse and Human Immunology, J. of Immunology, 172, pp. 2731-2738, 2004.

(56) References Cited

OTHER PUBLICATIONS

Mukasa et al., "Function analysis of folate receptor-β in a RA synovial membrane macrophage cell line" Rheumatoid, Japan College of Rheumatology, 40(2): 378, 2000.
Mulherin et al., "Synovial tissue macrophage populations and articular damage in rheumatoid arthritis", Arthritis and Rheumatism, vol. 39, No. 1, pp. 115-124, 1996.
Nagayoshi et al., "Arthritis and Reheumatism", vol. 52, pp. 2666-2675, Sep. 9, 2005.
Nair et al., "Folate Analogues Altered in the C9-N10 Bridge Region. 10-Oxafolic Acid and 10-Oxaaminopterin", Journal of Medicinal Chemistry, vol. 19, No. 6, pp. 825-829, 1976.
Nair et al., "Folate Analogues Altered in the C9-N10 Bridge Region: N10-Tosylisohomofolic Acid and N10-Tosylisohomoaminopterin", Journal of Medicinal Chemistry, vol. 21, No. 7, pp. 673-677, 1978.
Nair et al., "Folate Analogues Altered in the C9-N10 Bridge Region: 11-Thiohomofolic Acid", Journal of Medicinal Chemistry, vol. 22, No. 7, pp. 850-855, 1979.
Nair et al., "Folate Analogues Altered in the C9-N10 Bridge Region. 14. 11-Oxahomofolic Acid, a Potential Antitumor Agent", Journal of Medicinal Chemistry, vol. 23, pp. 59-65, 1980.
Nair et al., Folate Analogues Altered in the C9-N10 Bridge Region. 18. Synthesis and Antitumor Evaluation of 11-Oxahomoaminopterin and Related Compounds, Journal of Medicinal Chemistry, vol. 24, pp. 1068-1073, 1981.
Nair et al., "Folate Analogues. 20. Synthesis and Antifolate Activity of 1, 2, 3, 4, 5, 6, -Hexahydrohomofolic Acid", Journal of Medicinal Chemistry, vol. 26, pp. 135-140, 1983.
Nair et al., "Folate Analogues. 21. Synthesis and Antifolate and Antitumor Activities of N10-(Cyanomethyl)-5,8-dideazafolic Acid", Journal of Medicianal Chemistry, vol. 26, pp. 605-607, 1983.
Nair et al., "Folate Analogues. 22. Synthesis and Biological Evaluation of Two Analogues of Dihydrofolic Acid Processing a 7,8-Dihydro-8-oxapterin Ring System" Journal of Medicinal Chemistry, vol. 26, 1164-1168, 1983.
Nakashima-Matsushita et al., Selective expression of folate receptor beta and its possible role in methotrexate transport in synovial macrophages from patients with rheumatoid arthritis, Arthritis Rheum. 42(8): 1609-1616, 1999.
Nezhat et al., "Four ovarian cancers diagnosised during laproscopic management of 1011 women with adnexal masses", Am J Obstet Gynecol., vol. 167, No. 3, pp. 790-796, 1992.
Oatis et al., "Synthesis of Quinazoline Analogues of Folic Acid Modified at Position 10", Journal of Medicinal Chemistry, vol. 20, No. 11, pp. 1393-1396, 1977.
Paigen et al., "Variation in susceptibility to atherosclerosis among inbred strains of mice", Atherosclerosis, vol. 57, No. 1, pp. 65-73, 1985.
Pasterkamp et al., "Techniques characterizing the coronary atherosclerotic plaque: Influence on clinical decision making?", J. Amer. Coll. Cardiol. 36:13-21, 2000.
Paulos et al., "Folate Receptor-Mediated Targeting of Therapeutic and Imaging Agents to Activated Macrophages in Rheumatoid Arthritis", Advanced Drug Delivery Reviews, vol. 56, No. 8, pp. 1205-1217, 2004.
Pelegrin et al., "Antibody-Fluorescein Conjugates for Photoimmunodiagnosis of Human Colon Carcinoma in Nude Mice", Institute of Biochemistry, University of Lausanne, vol. 67, No. 10, pp. 2529-2537, 1991.
Plante et al., "Polyglutamyl and Polylysyl Derivatives of the Lysine Analogues of Folic Acid and Homofolic Acid", Journal of Medicinal Chemistry, vol. 19, No. 11, pp. 1295-1299, 1976.
Rampone et al., "Ovarian cancer screening by transvaginal color Doppler ultrasonography", Minerva Ginecologica, vol. 53, Suppl. 1 al N 1, pp. 125-128, 2001.
Reddy et al., "Optimization of Folate-Conjugated Liposomal Vectors for Folate Receptor-Mediated Gene Therapy", J. Pharm. Sciences 88: 1112-1118, 1999.

Reddy et al., "Folate-Mediated Targeting of Therapeutic and Imaging Agents to Cancers", Critical Reviews in Ther. Drug Carrier Systems 15: 587-627, 1998.
Reddy et al., "Folate receptor specific anti-tumor activity of folate-mitomycin conjugates", Cancer Chemother. Pharmacol., 58(2): 229-36, 2006.
Reles et al., "Transvaginal Color Doppler Sonography and Conventional Sonography in the Preoperative Assessment of Adnexal Masses", Journal of Clinical Ultrasound, vol. 25, No. 5, pp. 217-225, Jun. 1997.
Roberts et al., "Folic Acid Analogs. Modifications in the Benzene-Ring Region. 3. Neohomofolic and Neobishomofolic Acids. An Improved Synthesis of Folic Acid and Its Analogs". Journal of Medicinal Chemistry, 16(6): 697-699, 1973.
Roberts et al., "Folic Acid Analogs. Modifications in the Benzene-Ring Region. 2. Thiazole Analogs", Journal of Medicinal Chemistry, 15 (12): 1310-1312, 1972.
Roberts et al., "Folic Acid Analogs. Modifications in the Benzene-Ring Region. 1. 2'- and 3'-Azafolic Acids", Journal of Medicinal Chemistry, 14(2): 125-130, 1971.
Roberts et al., "Folic Acid Analogs. Modifications in the Benzene-Ring Region. 4. 3'-Ethyl- and 3'-Isopropylfolic Acids", Journal of Medicinal Chemistry, vol. 17, No. 2, pp. 219-222, 1974.
Rouzi et al., "Lapascopic Ovarian Cystectomy: Selection of Patients and Consequences of Rupture of Ovarian Malignancy", Annals of Saudi Medicine, vol. 17, No. 3, pp. 321-325, 1997.
Rudd et al., "Imaging Atherosclerotic Plaque Inflammation with [<18>F]-Fluorodeoxyglucose Positron Emission Tomography", Circulation, vol. 105, No. 23, pp. 2709-2710, 2002.
Sato et al., "Usefulness of Mass Screening for Ovarian Carcinoma Using Transvaginal Ultasonography", American Cancer Society, vol. 89, No. 3, pp. 582-588, 2000.
Sevick-Muraca et al., "Fluorescence and Absorption Contrast Mechanisms for Biomedical Optical Imaging Using Frequency-Domain Techniques", Photochemistry and Photobiology, vol. 66, No. 1, pp. 55-64, 1997.
Sheski et al., "Endoscopic Treatment of Early-Stage Lung Cancer", Division of Pulmonary, Allergy, Care, and Occupational Medicine at IU School of Medicine, vol. 7, No. 1, pp. 35-44, Feb. 2000.
Shoup et al., "Synthesis of Fluorine-18-Labeled Biotin Derivatives: Biodistribution and Infection Localization", J. Nuclear Medicine, vol. 35, No. 10, pp. 1685-1690, 1994.
Sijtsema et al., "Confocal Direct Imaging Raman Microscope: Design and Application in Biology", Applied Spectroscopy, vol. 52, Issue 3, pp. 348-355, 1998.
Sima et al., "Experimental obstructive coronary atherosclerosis in the hyperlipidemic hamster", J Submicrosc Cytol Pathol, vol. 22, No. 1, pp. 1-16, 1990.
Simionescu et al., "Prelesional modifications of the vessel wall in hyperlipidemic atherogenesis: Extracellular accumulation of modified and reassembled lipoproteins", Ann. NY Acad. Sci., vol. 598, pp. 1-16, 1990.
Smart et al., "Protein kinase C activators inhibit receptor-mediated potocytosis by preventing internalization of caveolae", Journal of Cell Biology, vol. 124, No. 3, pp. 307-313, 1994.
Solomon et al., "Computerized Tomography in Ovarian Cancer", Gynecologic Oncology, vol. 15 pp. 48-55, 1983.
Sudimak et al., "Targeted drug delivery via the folate receptor", Advanced Drug Delivery Reviews, vol. 41, pp. 147-162, 2000.
Sundstrum et al., "Establishment and characterization of a human histiocytic lymphoma cell line (U-937)", International Journal of Cancer, vol. 17, No. 5, pp. 565-577, 1976.
Temple, Jr., et al., "Synthesis of Pseudo Cofactor Analogues as Potential Inhibitors of the Folate Enzymes", Journal of Medicinal Chemistry, vol. 25, pp. 161-166, 1982.
Toffoli et al., "Expression of Folate Binding Protein as a Prognostic Factor for Response to Platinum-Containing Chemotherapy and Survival in Human Ovarian Cancer", Int. J. Cancer, vol. 79, pp. 121-126, 1998.
Toffoli et al., "Overexpression of Folate Binding Protein in Ovarian Cancers", Int. J. Cancer (Pred. Oncol.), vol. 74, pp. 193-198, 1997.

(56) References Cited

OTHER PUBLICATIONS

Turk et al., "Folate-targeted imaging of activated macrophage in rats with adjuvant-induced arthritis", Arthritis and Rheumatism, vol. 46, No. 7, pp. 1947-1955, 2002.
Urban, "Screening for ovarian cancer: We now need a definitive randomized trial", BMJ, vol. 319, pp. 1317-1318, Nov. 20, 1999.
Van Noort et al., "Cell Biology of Autoimmune Diseases", International Review of Cytology, vol. 178, pp. 127-204, 1998.
Vo-Dinh et al., "In Vivo Cancer Diagnosis of the Esophagus Using Differential Normalized Fluorescence (DNF) Indices", Lasers in Surgery and Medicine, vol. 16, pp. 41-47, 1995.
Wang et al., "Chemokines and their role in cardiovascular diseases", TCM, vol. 8, pp. 169-174, 1998.
Wang et al., "Synthesis, Purification, and Tumor Cell Uptake of Ga-Deferoxamine-Folate, a Potential Radiopharmaceutical for Tumor Imaging", American Chemical Society, Bioconjugate Chem., 1996, 7(1): 56-62, 1996, 1970.
Weinstock et al., "Folic Acid Analogs. II. p-{[2,6-Diamino-8-purinyl)methyl]amino}-benzoyl-L-glutamic Acid and Related Compounds", Journal of Medicinal Chemistry, 13(5): 995-997, 1970.
Weissleder et al., "In vivo imaging of tumors with protease-activated near-infrared fluorescent probes", Nature Biotechnology, vol. 17, pp. 375-378, 1999.
Weitman et al., "The folate receptor in central nervous system malignancies of childhood", Journal of Neuro-Oncology, vol. 21, pp. 107-112, 1994.
Whitehurst et al., "Development of an alternative light source to lasers for biomedical applications", SPIE, vol. 2629, pp. 291-298, 1993.
Wu et al., "Expression of Folate Receptor Type a in Relation to Cell Type Malignancy, and Differentiation in Ovary, Uterus and Cervix", Cancer Epidemiology, Biomarkers & Prevention, vol. 8, pp. 775-782, Sep. 1999.
Yavorsky et al., Antiparticles:, Handbook on Physics, pp. 339-340, 1984.
Zeisel et al., "Choline, an Essential Nutrient for Humans", The Faseb Journal, vol. 5, No. 7, pp. 2093-2098, 1991.
Delaloye et al., "Tumor imaging with monoclonal antibodies", Seminars in Nuclear Medicine, 25:144-164, 1995.
Reubi, "The role of peptides and their receptors as tumor markers", Endocrinology & Metabolism Clinics of North America, 22: 917-939, 1993.
Garin-Chesa et al., "Trophoblast and ovarian cancer antigen LK26. Sensitivity and specificity in immunopathology and molecular identification as a folate-binding protein", American Journal of Pathology, 142: 557-567, 1993.
Patrick et al., "Folate receptors as potential therapeutic targets in choroid plexus tumors of SV40 transgenic mice", Journal of Neuro-Oncology, 32: 111-123, 1997.
Weitman et al., "Distribution of the folate receptor GP38 in normal and malignant cell lines and tissues", Cancer Research, 52: 3396-3401, 1992.
Mathias et al., "Indium-111-DTPA-folate as a potential folate-receptor-targeted radiopharmaceutical", Journal of Nuclear Medicine, 39: 1579-1585, 1998.
Acosta et al., "Chromoendoscopy—where is it useful?", Journal of Clinical Gastroenterology, 27:13-20,1998.
Fleischer, "Chromoendoscopy and magnification endoscopy in the colon", Gastrointestinal Endoscopy, 49: S45-49, 1999.
Stepp et al., "Fluorescence endoscopy of gastrointestinal diseases: basic principles, techniques, and clinical experience", Endoscopy, 30: 379-386, 1998.
Ballou et al., "Tumor detection and visualization using cyanine fluorochrome-labeled antibodies", Biotechnology Progress, 13: 649-658, 1997.
Licha et al., "Synthesis, characterization, and biological properties of cyanine-labeled somatostatin analogues as receptor-targeted fluorescent probes", Bioconjugate Chemistry, 12: 44-50, 2001.
Becker et al., "Receptor-targeted optical imaging of tumors with near-infrared fluorescent ligands", Nature Biotechnology, 19: 327-331, 2001.
Terpetschnig et al., "Synthesis of squaraine-N-hydroxysuccinimide esters and their biological application as long-wavelength fluorescent labels", Analytical Biochemistry, 217: 197-204, 1994.
Mujumdar et al., "Cyanine dye labeling reagents containing isothiocyanate groups", Cytometry, 10: 11-19, 1989.
Wang et al., "Design and synthesis of [111In]DTPA-folate for use as a tumor-targeted radiopharmaceutical", Bioconjugate Chemistry, 8: 673-679, 1997.
Dimartino et al., "Antiarthritic and immunoregulatory activity of spirogermanium", Journal of Pharmacology an Experimental Therapeutics, 236: 103-110, 1986.
Ross et al., "Differential regulation of folate receptor isoforms in normal and malignant tissues in vivo and in established cell lines. Physiologic and clinical implications", Cancer, 73: 2432-2443, 1994.
Ross et al., "Folate receptor type beta is a neutrophilic lineage marker and is differentially expressed in myeloid leukemia", Cancer, 85: 348-357, 1999.
Curtin et al., "Stage IV ovarian cancer: impact of surgical debulking", Gynecologic Oncology, 64: 9-12, 1997.
Munkarah et al., "Prognostic significance of residual disease in patients with stage IV epithelial ovarian cancer", Gynecologic Oncology, 64: 13-17, 1997.
Murolo et al., "Ultrasound examination in ovarian cancer patients. A comparison with second look laparotomy", Journal of Ultrasound in Medicine, 8: 441-443, 1989.
Piver et al., "Second-look laparoscopy prior to proposed second-look parotomy", Obstetrics and Gynecology, 55: 571, 1980.
Bell et al., "Intraoperative radioimmunodetection of ovarian cancer using monoclonal antibody B72.3 and a portable gamma-detecting probe", Obstetrics and Gynecology, 76: 607-677, 1990.
Reuter et al., "Detection of colorectal carcinomas by intraoperative RIS in addition to preoperative RIS: surgical and immunohistochemical findings", European Journal of Nuclear Medicine, 19: 102-109, 1992.
Hornung et al., "Minimally-invasive debulking of ovarian cancer in the rat pelvis by means of photodynamic therapy using the pegylated photosensitizer PEG-m-THPC", British Journal of Cancer, 81: 631-637, 1999.
Folli et al., "Immunophotodiagnosis of colon carcinomas in patients injected with fluoresceinated chimeric antibodies against carcinoembryonic antigen", Proceedings of the National Academy of Sciences of the United States of America, 89: 7973-7977, 1992.
Folli et al., "Antibody-indocyanin conjugates for immunophotodetection of human squamous cell carcinoma in nude mice", Cancer Research, 54: 2643-2649, 1994.
Bannwarth et al., "Methotrexate in rheumatoid arthritis. An update", Drugs, 47: 25-50, 1994.
Bettegowda, et al., Proc. Natl. Acad. ScL U.S.A., 102: 1145-1150, 2005.
Bunce, et al., Infect. Immun., 60: 2636-2640, 1992.
Claassen E. et al., "Preparation and characteristics of dichloromethylene diphosphonate-containing liposomes," J. Microencapsul., 3: 109-14, 1986.
Marceau et al., Bioorganics and Medical Chemistry Letters, 15(24): 5442-5445, 2005.
Novabiochem® Letters, "Resins for the synthesis of biotinylated and fluorescently-labeled peptides," Jan. 2004, pp. 1-4, 2004.
Novabiochem® Letters, "Products for peptide ligation," Feb. 2004, pp. 1-4, 2004.
Novabiochem® Letters, "Amino acids for Fmoc SPPS," Mar. 2004, pp. 1-4, 2004.
Novabiochem® Letters, "PEG reagents," Apr. 2004, pp. 1-4, 2004.
International Search Report and Written Opinion for PCT/US2008/053293 completed Mar. 10, 2009.
Bettio, Andrea, et al., "Synthesis and Preclinical Evaluation of a Folic Acid Derivative Labeled with $^{18}$F for PET Imaging of Folate Receptor-Positive Tumors", Jul. 2006, The Journal of Nuclear Medicine, vol. 47, No. 7, pp. 1153-1160.
Chen, Xiaoyuan, et al., "MicroPET Imaging of Brain Tumor Angiogenesis with $^{18}$F-Labeled PEGylated RGD Peptide", Aug.

(56) References Cited

OTHER PUBLICATIONS

2004, *European Journal of Nuclear Medicine and Molecular Imaging*, vol. 31, No. 8, pp. 1081-1089.
Degrado, Timothy, et al., "Synthesis and Evaluation of $^{18}$F-Labeled Choline as an Oncologic Tracer for Positron Emission Tomography: Initial Findings in Prostate Cancer", Jan. 1, 2000, *Cancer Research*, pp. 110-117.
Marecos et al., "Antibody-Mediated versus Nontargeted Delivery in a Human Small Cell Lung Carcinoma Model", Bioconiugate Chemistry, 9:184-191 (1998).
"Osteomyelitis", XP-002569963, URL:http://emedicine.medscape.com/article/785020-overview>, retrieved Feb. 22, 2010.
Kennedy MD, "Folate-targeted imaging agents," Thesis submitted to the faculty of Purdue University in partial fulfillment of the requirements for the degree of Doctor of Philosophy, published Nov. 2004.
Holladay et al., "Riboflavin-mediated delivery of a macromolecule into cultured human cells," *Biochim Biophys Acta* 1426(1): 195-204 (1999).
Low PS, Leamon CP, Reddy JA, Green MA, Mathias C, Turk MJ, Waters DJ, Lu J, Lee RJ, Kennedy MD, "Folate-mediated delivery of therapeutic and imaging agents to cancer tissue," Gene, Drug Therapy, and Molecular Biology (Abstract), 2000.
Low, P.S., Leamon, C.P., Reddy, J.A., Green, M.A., Mathias, C., Turk, M.J., Waters, D.J., Lu, J., Lee, R.J. and Kennedy, M., "Folate-Mediated Delivery of Therapeutic and Imaging Agents to Cancer Tissues In Vivo," International Symposium on Tumor Targeted Delivery Systems, Bethesda, Maryland. British Journal of Pharmacology, vol. 134 (Abstract), 2001.
Kern, et al., "Evaluation of the Culprit Plaque and the Physiological Significance of Coronary Atherosclerotic Narrowings," Circulation, 2001; 103:3142-3149.
Phelps et al., Journal of Nuclear Medicine, 1975, 16(3): 210-224.
Snook et al., Br. J. Cancer, 1990, 62 (Suppl. X): 89-91.
U.S. Appl. No. 60/956,489, filed Aug. 17, 2007, Low et al.
Patton, Radiographics, 1998, 18: 995-1007.
Kanagaki et al., "Pituitary Gland and Parasellar Region," in *Magnetic Resonance Tomography*, Reiser et al. (eds.), 2008, p. 422.
Barnes, H. H., et al., "Purification of Catechol Siderophores by Boronate Affinity Chromatography: Identification of Chrysobactin From *Erwinia carotovora* subsp. *carotovora*", 1999, *BioMetals*, vol. 12, pp. 83-87.
Collins, Peter, et al., "Monosaccharides, Their Chemistry and Their Roles in Natural Products", 1995 *Wiley Publishers*, Book Reference, We will provide the book if requested.
Georgakoudi, Irene, et al., "In Vivo Flow Cytometry: A New Method for Enumerating Circulating Cancer Cells", Aug. 1, 2004, *Cancer Research*, No. 64, pp. 5044-5047.
Hanessian, Stephen, "Preparative Carbohydrate Chemistry", 1997 *Marcel Dekker, Inc.*, Book Reference, We will provide the book if requested.
Idanpaan-Heikkila, Ilona, et al., "Oligosaccharides Interfere With the Establishment and Progression of Experimental Pneumococcal Pneumonia", 1997, *The Journal of Infectious Diseases*, No. 176, pp. 704-712.
Iijima, Masatomi, et al., "IC202A, A New Siderophore With Immunosuppressive Activity Produced by *Streptoalloteichus* sp. 1454-19. I. Taxonomy, fermentation, isolation and biological activity.", Jan. 1999, *The Journal of Antibiotics* (Toyko), vol. 52, No. 1, pp. 20-24.
Lingwood, Clifford A., "Oligosaccharide Receptors for Bacteria: A View to a Kill", 1998, *Curr Opin Chem Biol.*, pp. 695-700.
Michelson, Alan D., et al., "Evaluation of Platelet Function by Flow Cytometry", 2000, *Methods*, vol. 21, pp. 259-270.
Novak, J., et al., "In Vivo Flow Cytometer for Real-Time Detection and Quantification of Circulating Cells", Jan. 1, 2004 *Optics Letters*, vol. 29, No. 1, pp. 77-79.
Ratledge, Colin, et al., "The Occurrence of Carboxymycobactin, The Siderophore of Pathogenic Mycobacteria, As a Second Extracellular Siderophore in *Mycobacterium smegmatis*", 1996 *Microbiology*, vol. 142, pp. 2207-2212.
Scharfman, Andree, et al., "*Pseudomonas aeruginosa* Binds to Neoglycoconjugates Bearing Mucin Carbohydrate Determinants and Predominantly to sialyl-Lewis x Conjugates", 1999, *Glycobiology*, vol. 9, No. 8, pp. 757-764.
Schalk, Isabelle J., et al., "Iron-Free Pyoverdin Binds to Its Outer Membrane Receptor FpvA in *Pseudomonas Aeruginosa*: A New Mechanism for Membrane Iron Transport", 2001, *Molecular Microbiology*, vol. 39, No. 2, pp. 351-360.
Albrecht-Gary et al., "Bacterial Iron Transport: Coordination Properties of Pyoverdin PaA, a Peptidic Siderophore of *Pseudomonas aeruginosa*", 1994. *Inorg. Chem.*, 33 (26), pp. 6391-6402.
Henne, Walter A., et al., "Synthesis and Activity of a Folate Peptide Camptothecin Prodrug", (Aug. 9, 2006), *Bioorganic & Medicinal Chemistry Letters*, vol. 16, pp. 5350-5355.
Tang, Hailun, et al., "Prostate Targeting Ligands Based on N-Acetylated α-Linked Acidic Dipeptidase", (2003), *Biochemical and Biophysical Research Communications*, vol. 307, pp. 8-14.
Wosikowski, Katja, et al., "In Vitro and in Vivo Antitumor Activity of Methotrexate Conjugated to Human Serum Albumin in Human Cancer Cells", (May 2003), *Clinical Cancer Research*, vol. 9, pp. 1917-1926.
International Search Report and Written Opinion for PCT/US2007/023176 completed Aug. 4, 2008 (Apr. 8, 2008).
Wiener et al., "Targeting Dendrimer-Chelates to Tumors and Tumor Cells Expressing the High-Affinity Folate Receptor," *Investigative Radiology*, 1997; 32(12):748-754.
Paulos et al., "Ligand Binding and Kinetics of Folate Receptor Recycling in Vivo: Impact on Receptor-Mediated Drug Delivery," Molecular Pharmacology, 2004; 66:1406-1414.
He et al., "In vivo quantitation of rare circulating tumor cells by multiphoton intravital flow cytometry," Proc Nat Acad Sci USA, 2007; 104: 11760-11765.
Chen et al., "In vivo imaging of proteolytic activity in atherosclerosis," Circulation, 2002, 105: 2766-2771.
Mathias et al., "Synthesis of [99mTc]DTPA-Folate and Its Evaluation as a Folate-Receptor-Targeted Radiopharmaceutical", Bioconj. Chem., 2000; 11:253-257.
Linder et al., "In Virto & In Vivo Studies with α-and y-Isomers of 99mTc-OXA-Folate Show Uptake of Both Isomers in Folate-Receptor (+) KB Cell Lines", Soc. Nucl. Med. Proc., May 2000; 41:5:119.
Ilgan et al., "99mTc-Ethylenedicysteine-Folate: A New Tumor Imaging Agent. Synthesis, labeling and Evaluation in Animals", Can. Biother. & Radiophar., 1998; 13:6:427-435.
Massoud et al., "Molecular imaging in living subjects: seeing fundamental biological processes in a new light", 2003, Genes Dev. 17: 545-580.
Caliceti et al., "Pharmacokinetic and biodistibution properties of poly9ethylene glycol)—protein conjugates", 2003, Adv. Drug Del. Rev. 55: 1261-1277.
Tamaki et al., "PET in Oncology" Jpn J Cancer Clin, 2003, 49(6): 531-535.
Remington: The Science & Practice of Pharmacy, 21th Edition (Lippincott Williams & Wilkins, 2005).
Bendele et al., "Animal Models of Arthritis: Relevance to Human Disease", Toxicology Pathology, vol. 27, No. 1, pp. 134-142, 1999.
Tanaka et al., Journal of Japanese Society of Gastroenterology 91(2) 131-135, 1994 (English Trans.).
Tanaka et al., Journal of Japanese Society of Gastroenterology 91(2) 131-135, 1994 (Japanese).

* cited by examiner

POSITRON EMISSION TOMOGRAPHY IMAGING METHOD

CROSS-REFERENCE TO RELATED APPLICATIONS

This application is a U.S. national counterpart application of international application serial no. PCT/US2008/053293 filed Feb. 7, 2008, under 35 USC §371, which claims the benefit of U.S. Provisional Patent Application No. 60/899,921, filed Feb. 7, 2007, and U.S. Provisional Patent Application No. 60/896,018, filed Mar. 21, 2007, under 35 USC §119(e), all of which are incorporated herein by this reference in their entirety.

TECHNICAL FIELD

This invention relates to compositions and methods to diagnose and/or monitor pathogenic disease states using positron emission tomography. In particular, this invention relates to pathogenic cells that uniquely express, preferentially express, or overexpress vitamin receptors. Vitamin receptor binding compounds conjugated to a radiophore useful in positron emission tomography are described for diagnosing and/or monitoring disease states using an extra-corporeal device.

BACKGROUND

Vitamin receptors are overexpressed on cancer cells. For example, the folate receptor, a 38 KD GPI-anchored protein that binds the vitamin folic acid with high affinity (<1 nM), is overexpressed on many malignant tissues, including ovarian, breast, bronchial, and brain cancers. In particular, it is estimated that 95% of all ovarian carcinomas overexpress the folate receptor. In contrast, with the exception of kidney, choroid plexus, and placenta, normal tissues express low or nondetectable levels of the folate receptor. Most cells also use an unrelated reduced folate carrier to acquire the necessary folic acid.

Following receptor binding of vitamins such as folate to vitamin receptors, rapid endocytosis delivers the vitamin into the cell, where it is unloaded in an endosomal compartment at lower pH. Importantly, covalent conjugation of small molecules, proteins, and even liposomes to vitamins and other vitamin receptor binding ligands does not block the ability of the ligand to bind to its receptor, and therefore, such ligand conjugates can readily be delivered to and can enter cells by receptor-mediated endocytosis.

It has also been shown that activated monocytes overexpress the folate receptor. The overexpression of folate receptors on activated macrophages, and on activated monocytes, is described in U.S. Patent Application No. 60/696,740 and U.S. Patent Application Publication No. US 2002/0192157, each entirely incorporated herein by reference. Further, it has also been reported that the folate receptor β, the nonepithelial isoform of the folate receptor, is expressed on activated, but not resting, synovial macrophages. Activated macrophages can participate in the immune response by nonspecifically engulfing and killing foreign pathogens within the macrophage, by displaying degraded peptides from foreign proteins on the macrophage cell surface where they can be recognized by other immune cells, and by secreting cytokines and other factors that modulate the function of T and B lymphocytes, resulting in further stimulation of immune responses. However, activated macrophages can also contribute to the pathophysiology of disease in some instances. For example, activated macrophages can contribute to atherosclerosis, rheumatoid arthritis, autoimmune disease states, and graft versus host disease, among other disease states.

An example of the contribution of activated macrophages to disease states is the involvement of activated macrophages in the progression of atherosclerosis. Atherosclerosis is a disease state initiated when a fatty streak forms within a blood vessel wall. Formation of fatty streaks is believed to result from accumulation of lipoprotein particles in the intima layer of the blood vessel wall, the layer of the vessel wall underlying the luminal endothelial cell layer. Lipoprotein particles can associate with extracellular matrix components in the intima layer and can become inaccessible to plasma antioxidants, resulting in oxidative modification of the lipoprotein particles. Such oxidative modification may trigger a local inflammatory response resulting in adhesion of activated macrophages and T lymphocytes to the luminal endothelium followed by migration into the intima layer. The oxidized lipoprotein particles themselves can act as chemo-attractants for cells of the immune system, such as macrophages and T cells, or can induce cells in the vascular wall to produce chemo-attractants. The atherosclerotic lesion may then form a fibrous cap with a lipid-rich core filled with activated macrophages. Atherosclerotic lesions that are unstable are characterized by local inflammation, and lesions that have ruptured and have caused fatal myocardial infarction are characterized by an infiltration of activated macrophages and T lymphocytes.

U.S. Pat. No. 6,782,289, U.S. Patent Application Publication No. US 2005/0244336, and PCT International Publication No. WO 2004/110250, each entirely incorporated herein by reference, provide discussions of possible origins of blood vessel disease. The references disclose catheter-based systems for detection of radio labeled conjugates that bind to activated macrophages within a blood vessel or other body lumen.

SUMMARY OF THE INVENTION

Described herein are compositions and methods to diagnose and/or monitor pathogenic disease states using positron emission tomography. Illustrative pathogenic disease states include cancers, disease states that involve activated macrophages or activated monocytes, disease states that involve activated plaques, and the like. The compositions and methods pertain to pathogenic cells that uniquely express, preferentially express, or overexpress vitamin receptors. In one embodiment, vitamins, or analogs thereof, conjugated to a radiophore are used to diagnose and/or monitor such disease states extra-corporeally using positron emission tomography.

In another embodiment, methods are described for diagnosing and/or monitoring a cancer wherein the cancer cells uniquely express, preferentially express, or overexpress vitamin receptors. The methods comprise the steps of administering to a patient being evaluated for the cancer an effective amount of a conjugate of the general formula B-L-X, wherein B comprises a vitamin, or an analog thereof, the group X comprises a radiophore, and L is an optional bivalent linker. The method includes allowing sufficient time for the vitamin conjugate to bind to the cancer cells, and diagnosing and/or monitoring the cancer extra-corporeally using positron emission tomography.

In another embodiment, methods are described for diagnosing and/or monitoring a disease state mediated by activated monocytes or activated macrophages having accessible binding sites for a vitamin. The methods comprise the steps of administering to a patient being evaluated for the disease state an effective amount of a conjugate of the general formula B-L-X, wherein B comprises a vitamin, or an analog thereof, the group X comprises a radiophore, and L is an optional bivalent linker. The method includes allowing sufficient time for the vitamin conjugate to bind to activated monocytes or activated macrophages, and diagnosing and/or monitoring the disease state extra-corporeally using positron emission tomography.

In another embodiment, methods are described for diagnosing and/or monitoring active atherosclerotic plaques associated with blood vessels wherein the plaques comprise activated macrophages having accessible binding sites for a vitamin. The methods comprise the steps of administering to a patient being evaluated for atherosclerosis an effective amount of a conjugate of the general formula B-L-X, wherein B comprises a vitamin, or an analog thereof, the group X comprises a radiophore, and L is an optional bivalent linker. The method includes allowing sufficient time for the vitamin conjugate to bind to activated macrophages associated with active plaques, and diagnosing and/or monitoring the active plaques extra-corporeally using positron emission tomography.

In another embodiment, compounds are described having the formula B-L-X, wherein B comprises a vitamin, or an analog thereof, the group X comprises a radiophore, and L is an optional bivalent linker. In one aspect, the radiophore is a positron-emitting isotope, wherein the isotope emits a pair of annihilation photons moving in opposite directions that result from positron annihilation with an electron. In another aspect, the radiophore decays with a half-life of about 80 minutes to about 8 hours by emission of positrons.

In another embodiment, compositions are described comprising a compound of formula B-L-X, wherein B comprises a vitamin, or an analog thereof, the group X comprises a radiophore, and L is an optional bivalent linker. In one aspect, the radiophore is a positron-emitting isotope, wherein the isotope emits a pair of annihilation photons moving in opposite directions that result from positron annihilation with an electron. In another aspect, the radiophore has a half-life of about 80 minutes to about 8 hours.

The compounds and compositions described herein may be used with any of the methods described herein.

In one embodiment of the compounds described herein, the conjugate B-L-X is of the formula

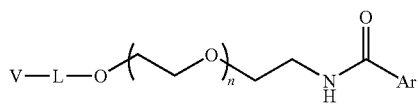

wherein V is a vitamin receptor binding moiety, or an analog or derivative thereof; L is an optional bivalent linker; n is an integer selected from 1 to about 100; Ar is an aryl group, including heteroaryl groups, that includes one or more substituents $(R^f)_m$ comprising a radiophore or a precursor to a radiophore. In one aspect, $R^f$ includes one or more substituents, where at least one of said substituents is a intro or a fluoro; and m is an integer selected from 1 to about 3. In another aspect, Ar is a precursor for preparing an $^{18}F$ fluoroaryl radiophore, and accordingly $R^f$ comprises one or more nitro groups. In another aspect, Ar is an $^{18}F$ fluoroaryl radiophore where $R^f$ comprises one or more fluoro groups. It is therefore to be understood that in aspects where the integer m is greater than 1, $R^f$ may include more then one intro group, or $R^f$ may include both fluoro and nitro, or $R^f$ may include more than one fluoro group. It is also to be understood that the fluorine isotopes found in the various embodiments and aspects, and variations described herein may be selected from $^{18}F$ and $^{19}F$, or isotopic combinations thereof.

In another embodiment of the compounds described herein, the conjugate B-L-X is of the formula

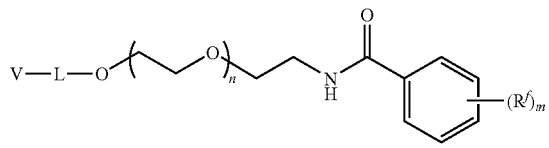

wherein V is a vitamin receptor binding moiety, or an analog or derivative thereof; L is an optional bivalent linker; n is an integer selected from 1 to about 100; $R^f$ is as defined in the various embodiments herein; and m is an integer selected from 1 to about 3.

In another embodiment of the compounds described herein, the conjugate B-L-X is of the formula

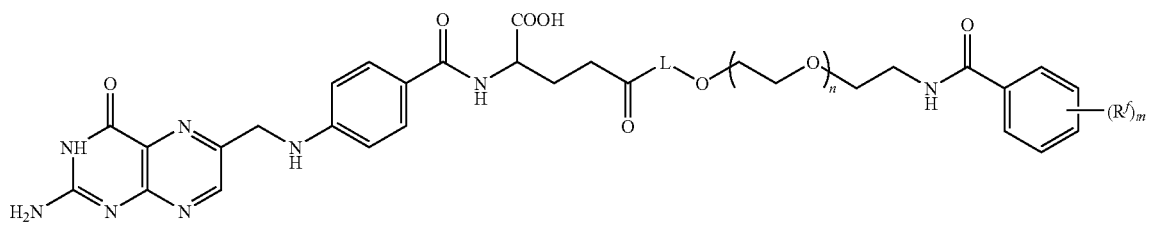

wherein L is an optional bivalent linker; n is an integer selected from 1 to about 100; $R^f$ is as defined in the various embodiments herein; and m is an integer selected from 1 to about 3.

It is to be understood that in the foregoing illustrative embodiments of the compounds B-L-X described herein, one or more asymmetric carbons may be present. Accordingly, described herein are each of the various stereochemical variants of those asymmetric carbons. Specific enantiomers and diastereomers, specific racemic mixtures, and various mixtures and combinations of each of the foregoing are described herein.

In another embodiment, methods are described for preparing a conjugate of the formula B-L-X, wherein B comprises a vitamin, or an analog thereof, L is an optional bivalent linker, and the group X comprises a radiophore. In one aspect, the radiophore decays with a half-life of about 80 minutes to about 8 hours by emission of positrons, and where the radiophore emits a pair of annihilation photons moving in opposite directions resulting from positron annihilation with an electron. The methods comprise the steps of providing the vitamin, in a reactive form capable of reacting with a radiophore in reactive form, providing the radiophore in the reactive form capable of reacting with the vitamin in reactive form, and contacting the reactive form of the vitamin with the reactive form of the radiophore. In one variation, each of the reactive forms of the vitamin, or analog or derivative thereof, and the radiophore are reacted with a reactive form of a bivalent linker. It is appreciated that such chemical steps may be performed in various sequences, and may include optional protecting groups.

In another embodiment, methods are described for preparing $^{18}$F radiolabeled and/or $^{19}$F compounds from the corresponding nitro compounds. The methods include the step of reacting a conjugate of a nitroaryl precursor with an $^{18}$F and/or $^{19}$F fluorinating agent.

In another embodiment, kits are described herein for preparing $^{18}$F radiolabeled and/or $^{19}$F compounds for use in PET imaging. The kits comprise a conjugate of arylnitro precursor, an $^{18}$F and/or $^{19}$F fluorinating agent, an optional solvent, and a reaction container for reacting the arylnitro precursor with the fluorinating agent. In one variation, the kits also include a purification system. In one variation, the kits itself does not include the fluorinating agent, but rather, the fluorinating agent is generated prior to use with the kit, such as through the use of a cyclotron or other generator.

DETAILED DESCRIPTION

Figure 1:
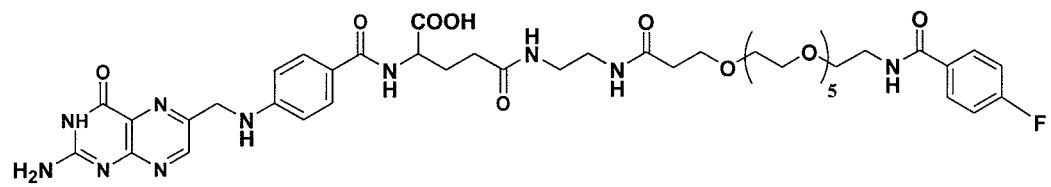
FIG. 1 shows an illustrative example of the $^{18}$F conjugates of folic acid described herein.
Figure 2:
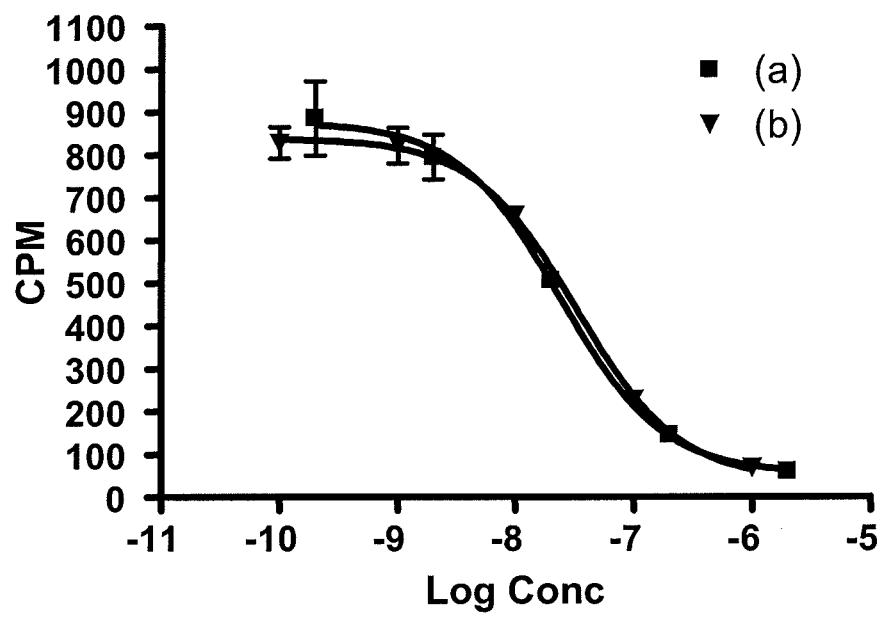
FIG. 2 shows the competitive binding of the compound of FIG. 1 compared to folic acid at folate receptors on KB cells: (a) compound of FIG. 1, $K_d$=23.8 nM; (b) folic acid, $K_d$=32.7 nM. The relative affinity of the compound of FIG. 1 compared to folic acid is 1.37. The compound of FIG. 1 shows a serum binding of 12.2%.

The present invention relates to compositions and methods to diagnose and/or monitor pathogenic disease states using positron emission tomography (PET), wherein the pathogenic cells uniquely express, preferentially express, or overexpress vitamin receptors or other receptors. The invention is applicable to populations of pathogenic cells that cause a variety of pathologies such as cancer, disease states that involve activated macrophages or activated monocytes, disease states that involve activated plaques, and the like. In the case of cancer, the population of pathogenic cells may be a cancer cell population that is tumorigenic, including benign tumors and malignant tumors, or it can be non-tumorigenic. The cancer cell population may arise spontaneously or by such processes as mutations present in the germline of the patient or somatic mutations, or it may be chemically, virally, or radiation induced. The invention can be utilized to diagnose and/or monitor such cancers as carcinomas, sarcomas, lymphomas, Hodgkin's disease, melanomas, mesotheliomas, Burkitt's lymphoma, nasopharyngeal carcinomas, leukemias, myelomas, and the like. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, lung, and other cancers.

The pathogenic cells can also be activated monocytes or macrophages associated with disease states such as fibromyalgia, rheumatoid arthritis, osteoarthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD), lupus erythematosus, Sjögren's syndrome, glomerulonephritis, inflammations of the skin, such as psoriasis, and the like, chronic inflammations, and inflammations due to injury, such as head or spinal cord injury, embolisms, and the like.

In one embodiment, a method is described for diagnosing and/or monitoring a disease state mediated by activated macrophages or activated monocytes having accessible binding sites for a vitamin. The method comprises the steps of administering to a patient being evaluated for the disease state an effective amount of a conjugate of the general formula B-L-X, wherein B comprises a vitamin, or an analog or derivative thereof capable of binding to a vitamin receptor, the group X comprises a radiophore, and L is an optional linker. The method includes allowing sufficient time for the conjugate to bind to activated monocytes or the activated macrophages, and diagnosing and/or monitoring the disease state extra-corporeally using positron emission tomography. In one aspect, the radiophore has a half-life of about 80 minutes to about 8 hours.

In another embodiment, a method is described for diagnosing and/or monitoring a cancer wherein the cancer cells uniquely express, preferentially express, or overexpress vitamin receptors. The method comprises the steps of administering to a patient being evaluated for the cancer an effective amount of a conjugate of the general formula B-L-X, wherein B comprises a vitamin, or an analog or derivative thereof capable of binding to a vitamin receptor, the group X comprises a radiophore, and L is an optional linker. In one aspect, the radiophore has a half-life of about 80 minutes to about 8 hours, and the method includes allowing sufficient time for the conjugate to bind to the cancer cells, and diagnosing and/or monitoring the cancer extra-corporeally using positron emission tomography.

In another embodiment, a method is described for diagnosing/monitoring active atherosclerotic plaques associated with blood vessels wherein the plaques comprise activated macrophages having accessible binding sites for a vitamin. The method comprises the steps of administering to a patient being evaluated for atherosclerosis an effective amount of a conjugate of the general formula B-L-X, wherein B comprises a vitamin, or an analog or derivative thereof capable of binding to a vitamin receptor, the group X comprises a radiophore, and L is an optional linker. In one aspect, the radiophore is capable of decaying by emission of positrons, and the method includes allowing sufficient time for the vitamin conjugate to bind to the activated macrophages associated with active plaques, and diagnosing and/or monitoring the active plaques extra-corporeally using positron emission tomography. In another aspect, the radiophore has a half-life of about 80 minutes to about 8 hours.

In this embodiment, the method relates to diagnosing and/or monitoring active atherosclerotic plaques in blood vessel walls. In one aspect, the ligand, such as a vitamin, or an analog or derivative thereof, binds to a receptor which is preferentially expressed, uniquely expressed, or overexpressed on the surface of activated macrophages relative to resting macrophages, is conjugated to a radiophore. The conjugates are administered to a patient being evaluated for atherosclerosis. The conjugates bind to activated macrophages associated with active atherosclerotic plaques. The radiation emitted by the radiophore is detected extra-corporeally using positron emission tomography. Accordingly, the conjugates can be used to distinguish active atherosclerotic plaques, containing activated macrophages, from inactive plaques wherein the plaques are present in the arteries or veins of a patient being evaluated for atherosclerosis.

It is understood that many unstable, i.e., active, atherosclerotic plaques are capable of rupturing and causing acute atherosclerotic syndromes. Even so, such atherosclerotic plaques may not in all cases produce luminal narrowing of blood vessels, particularly in the coronary circulation. Thus, the method of the present invention represents a significant advance in diagnosing and/or monitoring the risk of myocardial infarction, and in evaluating the need for clinical intervention, in patients suffering from atherosclerosis.

As described herein referring to compounds, the term "useful in positron emission tomography" means a compound that emits positron radiation capable of producing a pair of annihilation photons moving in opposite directions, the annihilation photons being produced as a result of positron annihilation with an electron. Those photons are capable of being detected by positron emission tomography (PET) using a suitable extra-corporeal device.

In one embodiment of the compounds described herein, the conjugate B-L-X is of the formula

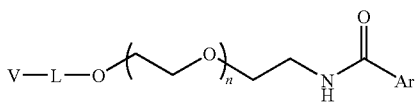

wherein V is a vitamin receptor binding moiety, or an analog or derivative thereof; L is an optional bivalent linker; n is an integer selected from 1 to about 100; Ar is an aryl group, including a heteroaryl group, that includes one or more substituents $(R^f)_m$ comprising a radiophore or a precursor to a radiophore, such as a nitro group and the like. In one variation, the integer n is in the range from 1 to about 20, or in the range from 3 to about 8.

In one aspect, $R^f$ includes one or more substituents, where at least one of said substituents is a nitro or a fluoro; and m is an integer selected from 1 to about 3. In another aspect, Ar is a precursor for preparing an $^{18}F$ fluoroaryl radiophore, and accordingly $R^f$ comprises one or more nitro groups. In another aspect, Ar is an $^{18}F$ fluoroaryl radiophore where $R^f$ comprises one or more fluoro groups. It is therefore to be understood that in aspects where the integer m is greater than 1, $R^f$ may include more then one nitro group, or $R^f$ may include both fluoro and nitro, or $R^f$ may include more than one fluoro group. It is also to be understood that the fluorine isotopes found in the various embodiments and aspects, and variations described herein may be selected from $^{18}F$ and $^{19}F$, or isotopic combinations thereof.

The vitamins, or analogs or derivatives thereof, or other ligands conjugated to a radiophore useful in PET, are used to diagnose and/or monitor disease states using an extra-corporeal device. PET detection using an extra-corporeal device is also referred to as a "PET scan," and devices for extra-corporeal detection using PET are well known in the art.

In accordance with embodiments where the conjugates bind to activated monocytes or macrophages, the conjugates can be formed from a wide variety of ligands and radiophores, including any ligand that binds to a receptor overexpressed, uniquely expressed, or preferentially expressed on the surface of activated monocytes or activated macrophages that is not expressed or presented or is not present in significant amounts on the surface of resting monocytes or macrophages. For activated macrophages, such ligands include N-formyl peptides, such as formyl-Met-Leu-Phe, high mobility group factor 1 protein (HMGB1), hyaluronan (also referred to as hyaluronic acid and/or hyaluronate), and fragments thereof, heat shock proteins, including HSP-70, toll-like receptor ligands, scavenger receptor ligands, co-receptors for antigen presentation, ligands that bind to the CD68, BER-MAG3, RFD7, CD4, CD 14, and HLA-D markers on activated macrophages, ligands that bind to urokinase plasminogen activator receptors, such as the WX-360 peptide, antibodies, or fragments thereof, that bind preferentially to activated macrophages, and vitamins or receptor-binding vitamin analogs and derivatives.

For monocytes, the monocyte-binding ligand can be any ligand that binds to a receptor expressed or overexpressed on activated monocytes including CD40, CD16, CD14, CD11b, and CD62 binding ligands, 5-hydroxytryptamine, macrophage inflammatory protein 1-α, MIP-2, receptor activator of nuclear factor κB ligand antagonists, monocyte chemotactic protein 1-binding ligands, chemokine receptor 5 binding ligands, RANTES binding ligands, chemokine receptor-binding ligands, and vitamins or receptor-binding vitamin analogs and derivatives, and the like. The conjugates are capable of preferentially binding to activated monocytes or activated macrophages compared to resting monocytes or macrophages due to preferential expression of the receptor for the ligand on activated monocytes or macrophages.

In the above-described embodiments, the ligand, such as the vitamin or analog or derivative thereof, can be any ligand that binds to a receptor which is preferentially expressed, uniquely expressed, or overexpressed the surface of cancer cells, or activated monocytes or activated macrophages relative to resting monocytes or macrophages. Exemplary of such ligands are vitamins selected from the group consisting of folate receptor-binding ligands, biotin receptor-binding ligands, vitamin $B_{12}$ receptor-binding ligands, riboflavin receptor-binding ligands, thiamine receptor-binding ligands, and other vitamin receptor-binding ligands, or analogs or derivatives thereof.

Acceptable vitamin moieties that can be used in accordance with the invention include niacin, pantothenic acid, folic acid, riboflavin, thiamine, biotin, vitamin $B_{12}$, and the lipid soluble vitamins A, D, E and K. In one aspect, these vitamins, and their receptor-binding analogs and derivatives, constitute the targeting entity that can be coupled with a radiophore, capable of emitting radiation, to form the conjugates for use in accordance with the invention. One illustrative group of vitamin moieties includes folic acid, biotin, riboflavin, thiamine, vitamin $B_{12}$, and receptor-binding analogs and derivatives of these vitamin molecules, and other related vitamin receptor-binding molecules. Further illustrative vitamins and analogs and derivatives thereof are described in U.S. Pat. No. 5,688,488, entirely incorporated herein by reference.

In another embodiment, the vitamin receptor-binding ligand can be folic acid, a folic acid analog, or another folate receptor-binding molecule. Exemplary of a vitamin analog is a folate analog containing a glutamic acid residue in the D configuration, where it is understood that folic acid normally contains one glutamic acid in the L configuration linked to pteroic acid. Other analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroyl-glutamic acid (dichloromethotrexate).

In another aspect, compounds described herein are radiophores and emit radiation that is useful in diagnostic and/or monitoring methods employing positron emission tomography. The compounds emit positron radiation capable of producing a pair of annihilation photons moving in opposite directions, the annihilation photons are produced as a result of positron annihilation with an electron. In one aspect, the radiophore is generally a radioisotope linked to another chemical structure, such as aryl rings, including heteroaryl rings. In another aspect, the radiophore can comprise the radioisotope alone.

In any or all of the above-described embodiments, the radiophore may include a positron-emitting isotope having a suitable half-life and toxicity profile. In various embodiments, the radioisotope has a half-life of more than 30 minutes, more than 70 minutes, more than 80 minutes, more than 90 minutes, more than 100 minutes, less than 8 hours, less than 6 hours, less than 4 hours, or less than 3 hours. In other embodiments, the radioisotope has a half-life of about 30 minutes to about 4 hours, about 70 minutes to about 4 hours, about 80 minutes to about 4 hours, about 90 minutes to about 4 hours, about 100 minutes to about 4 hours, about 30 minutes to about 6 hours, about 70 minutes to about 6 hours, about 80 minutes to about 6 hours, about 90 minutes to about 6 hours, about 100 minutes to about 6 hours, about 30 minutes to about 8 hours, about 70 minutes to about 8 hours, about 80 minutes to about 8 hours, about 90 minutes to about 8 hours, or about 100 minutes to about 8 hours.

The compounds includes a useful positron emitting isotope. A suitable radiophore may be prepared using the fluorine isotope $^{18}$F. Other useful positron-emitting isotopes may also be employed, such as $^{34}$Cl, $^{45}$Ti, $^{51}$Mn, $^{61}$Cu, $^{63}$Zn, $^{82}$Rb, $^{68}$Ga, $^{66}$Ga, $^{11}$C, $^{13}$N, $^{15}$O, and $^{18}$F. In one illustrative embodiment, the radioisotope is selected from $^{64}$Cu, $^{68}$Ga, $^{66}$Ga, and $^{18}$F. Factors that may be included during selection of a suitable isotope include sufficient half-life of the positron-emitting isotope to permit preparation of a diagnostic composition in a pharmaceutically acceptable carrier prior to administration to the patient, and sufficient remaining half-life to yield sufficient activity to permit extra-corporeal measurement by a PET scan. Further, a suitable isotope should have a sufficiently short half-life to limit patient exposure to unnecessary radiation. In an illustrative embodiment, $^{18}$F, having a half-life of 110 minutes, provides adequate time for preparation of the diagnostic composition, as well as an acceptable deterioration rate. Further, on decay $^{18}$F is converted to $^{18}$O.

In one illustrative embodiment, the isotope should have sufficient chemical activity to permit the isotope to become bound to a chemical compound and in turn to the ligand, whether or not a linker is used. Isotopes of elements having toxic properties can be avoided. Positron-decaying isotopes having suitable half-lives include: $^{34}$Cl, half-life about 32 minutes; $^{45}$Ti, half-life about 3 hours; $^{51}$Mn, half-life about 45 minutes; $^{61}$Cu, half-life about 3.4 hours; $^{63}$Zn, half-life about 38 minutes; $^{82}$Rb, half-life about 2 minutes; $^{68}$Ga, half-life about 68 minutes, $^{66}$Ga, half-life about 9.5 hours, $^{11}$C, half-life about 20 minutes, $^{15}$O, half-life about 2 minutes, $^{13}$N, half-life about 10 minutes, or $^{18}$F, half-life about 110 minutes.

In illustrative embodiments, the radioisotope is covalently attached to an aromatic group, such as an aryl or heteroaryl group. Illustrative aryl and heteroaryl groups include benzamidyl, benzylic, phenyl, pyridinyl, pyrimidinyl, pyridazinyl, and like groups, other aromatic groups, including polycyclic aryl groups such as, naphthyl, benzothiazolyl, benzimizolyl, benzoxazolyl, and like groups. In one illustrative embodiment, the radioisotope is $^{18}$F and the radiophore includes an aryl group to which the radioisotope is covalently attached.

The conjugates can bind with high affinity to receptors on cancer cells or activated monocytes or activated macrophages. It is understood that the high affinity binding can be inherent to the ligand or the binding affinity can be enhanced by the use of a chemically modified ligand (i.e., an analog or a derivative) or by the particular chemical linkage, in the conjugate, between the ligand and the radiophore.

The chemical linkage in the conjugate between the ligand and the radiophore can be a direct linkage or can be through an intermediary linker. If present, an intermediary linker can be any biocompatible linker known in the art. Illustratively, the linker comprises a chain of about 1 to about 50 atoms selected from carbon, nitrogen, oxygen, and sulfur atoms. In one variation, the linker comprises a chain of about 5 to about 25 atoms. In alternate embodiments, the linkers described herein may also include phosphorus atoms. In another illustrative variation, the linker is a lower molecular weight linker, such as a linker having an approximate molecular weight less than about 1000, or illustratively in the range of about 30 to about 500. Additional illustrative linkers and linking methods useful in the compounds and methods described herein, including the synthetic preparation thereof, are described in U.S. patent application Ser. Nos. 10/765,336 and 60/590,580, each entirely incorporated herein by reference. Any other linkers or linking methods known in the art can also be used.

Generally, any manner of forming a conjugate between the ligand and the radiophore, or alternatively between an optional linker and the ligand, or between an optional linker and the radiophore can be utilized in the compounds and methods described herein. Alternatively, with or without a linker, the conjugate can be formed by conjugation of the components of the conjugate, for example, through hydrogen, ionic, or covalent bonds. Illustratively, covalent bonding of the components of the conjugate is used, for example, through the formation of ether, amino, amide, ester, disulfide, thiol, hydrazino, hydrazono, imino, and/or hydroxylimino bonds carbon fragments bearing the appropriate functionalities, such as between acid, aldehyde, hydroxy, amino, sulfhydryl, hydroxylamine, and/or hydrazine groups. Also, the linker can comprise an indirect means for associating the ligand with the radiophore, such as by connection through spacer arms or bridging molecules, or through the use of complexing agents that are incorporated into the conjugate. It is understood that neither direct nor indirect means for association of the radiophore with the receptor binding ligand in formation of the conjugates described herein should prevent the binding of the ligand to the receptor on the cancer cells or activated monocytes or activated macrophages for the desirable operation of the method of the present invention.

In another illustrative aspect, the linker contributes to water solubility of the conjugate, or at least does not materially detract from water solubility. Advantageous linkers for water solubility include water soluble polymers such as dextran, cellulose ethers, amino acid, oligopeptide and polypeptide linkers of varying lengths, and polyalkylene glycols, including polyethylene glycols of varying lengths. In another embodiment, such polymers have a molecular weight of less than about 1000, or have a molecular weight in the range of about 30 to about 500. In addition, linkers including carboxylic acid bearing amino acids, such as aspartic acid and glutamic acid, and linkers including amino groups, such as ornithine, lysine, and arginine are also described herein. In addition, highly water soluble linkers such as carbohydrate linkers, and linkers of carbohydrate analogs and derivatives, such as those described in U.S. provisional patent application Ser. No. 60/946,092, entirely incorporated herein by reference, may also be included in the optional linker L.

In another embodiment, the hydrophilic spacer linkers described herein include a polyether, such as the linkers of the following formulae:

In another illustrative embodiment, linkers are described that may also limit the rate of excretion of the conjugate from the patient by permitting the ligand to associate with the site of interest, such as cancer cells or activated monocytes or activated macrophages before being excreted in the bile from the liver, or in the urine. A linker may facilitate, or may delay metabolic consumption of the conjugate such as by retarding reticuloendothelial system uptake, particularly by the liver. A linker may also help avoid association of the conjugate with non-target organs, cells, fluids, or proteins. If, for example, the conjugate associated with a serum protein, the PET scan would provide a scan of the patient's blood vessels generally, in contrast to the specific location of cancer cells or activated monocytes or activated macrophages sought. Also, the linker

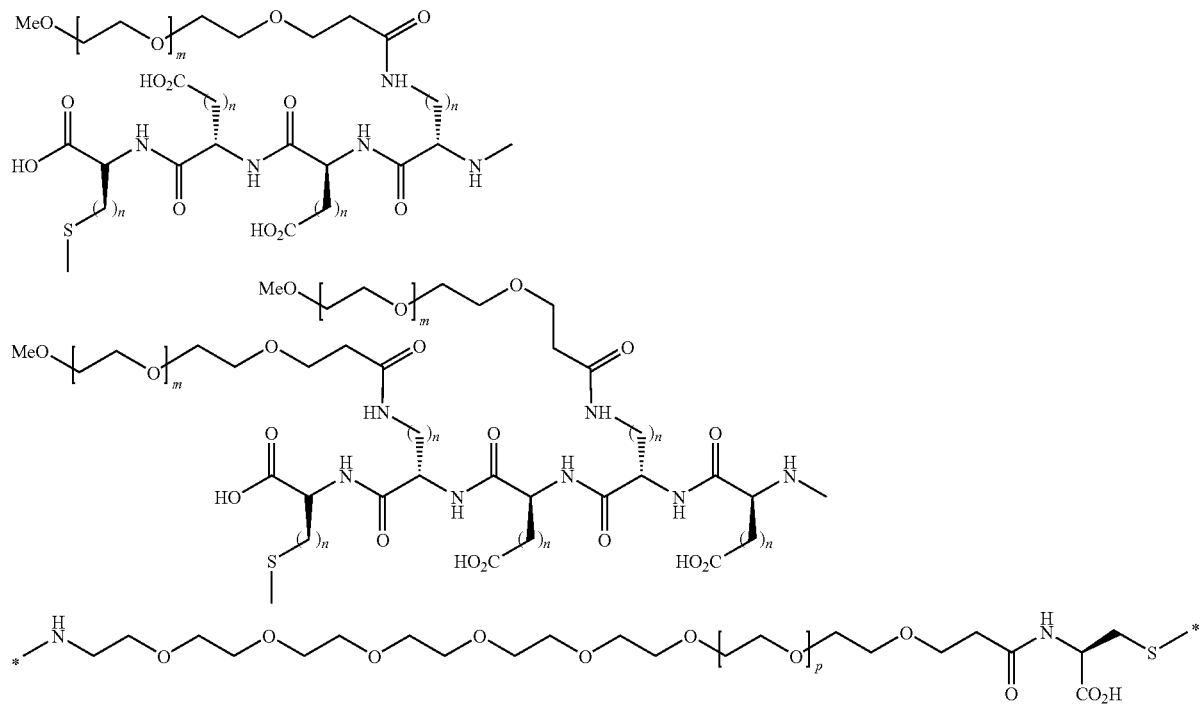

where m is an integer independently selected in each instance from 1 to about 8; p is an integer selected 1 to about 10; and n is an integer independently selected in each instance from 1 to about 3. In one aspect, m is independently in each instance 1 to about 3. In another aspect, n is 1 in each instance. In another aspect, p is independently in each instance about 4 to about 6. Illustratively, the corresponding polypropylene polyethers corresponding to the foregoing are contemplated herein and may be included in the conjugates as hydrophilic spacer linkers. In addition, it is appreciated that mixed polyethylene and polypropylene polyethers may be included in the conjugates as hydrophilic spacer linkers. Further, cyclic variations of the foregoing polyether compounds, such as those that include tetrahydrofuranyl, 1,3-dioxanes, 1,4-dioxanes, and the like are contemplated herein.

In another illustrative embodiment, the hydrophilic spacer linkers described herein include a plurality of hydroxyl functional groups, such as linkers that incorporate monosaccharides, oligosaccharides, polysaccharides, and the like. It is to be understood that the polyhydroxyl containing spacer linkers comprises a plurality of —(CROH)— groups, where R is hydrogen or alkyl.

may facilitate or accelerate a preferred route of excretion of the conjugate, such as through urine, for example, by encouraging the patient to drink significant fluids after the administration of the conjugate. In addition, it is understood that including a hydrophilic or plurality of hydrophilic groups on the linker may direct the conjugate to preferential clearance by the kidney rather than the liver.

In another embodiment of the compounds described herein, the conjugate B-L-X is of the formula

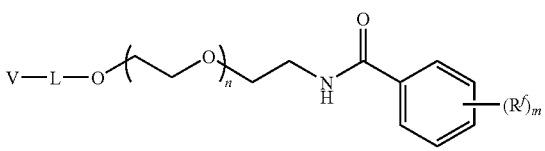

wherein V is a vitamin receptor binding moiety, or an analog or derivative thereof; L is an optional bivalent linker; n is an integer selected from 1 to about 100; $R^f$ is as defined in the various embodiments herein; and m is an integer selected from 1 to about 3. In one variation, the integer n is in the range from 1 to about 20, or in the range from 3 to about 8.

In another embodiment of the compounds described herein, the conjugate B-L-X is of the formula

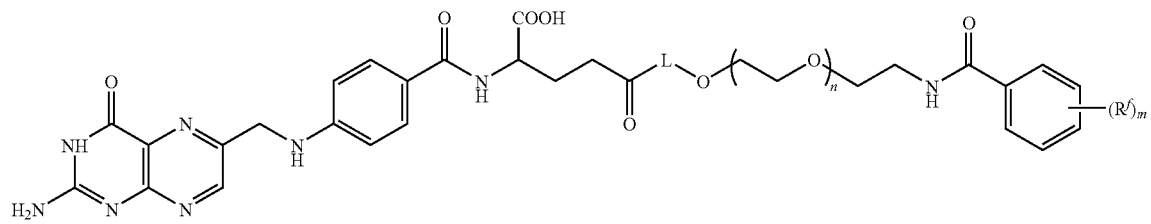

wherein L is an optional bivalent linker; n is an integer selected from 1 to about 100; $R^f$ is as defined in the various embodiments herein; and m is an integer selected from 1 to about 3. In one variation, the integer n is in the range from 1 to about 20, or in the range from 3 to about 8.

In the embodiment where the ligand is folic acid, an analog/derivative of folic acid, or any other folate receptor-binding molecule, the folate, or analog/derivative thereof, can be conjugated to the linker by an art-recognized procedure that utilizes trifluoroacetic anhydride to prepare γ-esters of folic acid via a pteroyl azide intermediate. This procedure results in the synthesis of folate, conjugated to the linker selectively through the γ-carboxy group of the glutamic acid groups of folate. Alternatively, folic acid analogs can be coupled by art-recognized procedures through the α-carboxy moiety of the glutamic acid group or both the a and γ carboxylic acid entities.

In embodiments where the linker includes one or more amino acids, including either or both naturally and non-naturally occurring amino acids, folic acid may be coupled to such amino acids, or peptide intermediates, to prepare folate linkers, and analogs and derivatives of folic acid, that may be coupled to the radiophore. Such amino acid coupling reactions may also be performed on resins, such as Merrifield resins, Wang resins, Universal resins, and the like. Additional details for processes of preparing peptide linker intermediates of pteroic acid and folic acid, and analogs and derivatives of each, are described in PCT international application publication WO 2006/071754, entirely incorporated herein by reference.

Illustratively, pteroic acid, or an analog or derivative thereof, is prepared by amidase or protease degradation of folic acid, or the corresponding analog or derivative thereof. For example, carboxypeptidase G, and like proteases, may be used. The resulting pteroic acid may be protected to allow for the selective functionalization of the alpha or gamma carboxylates, such as by protection of the N(10) amine. An illustrative synthesis is shown in the following scheme:

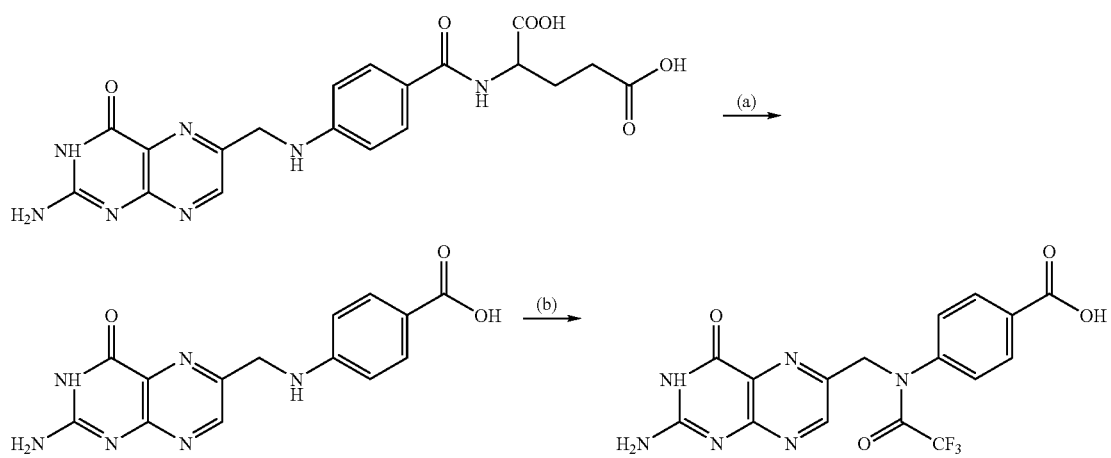

(a) Carboxypeptidase G, 0.1M Tris base/ZnCl$_2$; (b) (i) (F$_3$CCO)$_2$O, (ii) 3% TFA.

It is appreciated that analogs and derivatives of folic acid may be similarly converted into the corresponding analog or derivative of pteroic acid. Additional details for these processes are described in PCT international application no. PCT/US 2006/009153, entirely incorporated herein by reference.

In another illustrative embodiment of the compounds described herein, the pteroic acid, or analog of derivative thereof, may then illustratively be coupled to an optional linker, such as a peptide linker, a sugar or carbohydrate linker, a polyalkylene glycol linker, or other linker. In one illustrative embodiment, the pteroic acid compound, or analog or derivative thereof, is first attached to a suitable resin for subsequent solid-phase synthesis, as shown in the following scheme illustrated for a universal resin, where folate=N(10)-TFA pteroic-Glu(O-tBu):

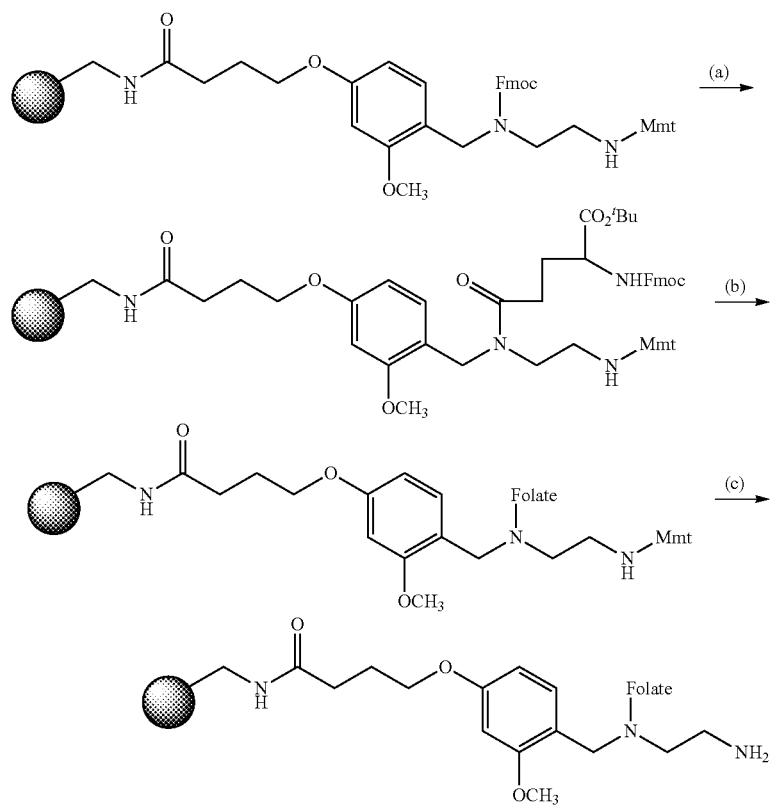

(a) 1) 20% piperidine in DMF, 2) Fmoc-Glu-OtBu, HATU, DIPEA/DMF; (b) 1) 20% piperidine in DMF, 2) N10 TFA-Pteroic, HATU, DIPEA/DMF; (c) 1M HOBt in DCM/TFE (1:1) to resin swollen in DCM It is appreciated that other solid-phase supports may be used, and that other pteroic acid and folic acid analogs and derivatives may be used as described herein.

In another illustrative embodiment of the compounds described herein, the solid supported pteroic acid or folic acid, or analog or derivative thereof, is attached to an optional linker, such as a PEG linker as shown in the following scheme, where n is an integer from 1 to about 100, from 1 to about 20, or is illustratively in the range from about 3 to about 8:

It is appreciated that PEG linkers of widely varying length, such as shorter lengths of 3 or 4 repeating units, or longer lengths of 6, 7, or 8 repeating units or significantly longer lengths of 10, 20, or 30 repeating units may be prepared according to this synthetic procedure.

In another illustrative embodiment of the compounds described herein, where the optional linker is a polyalkylene glycol, the solid supported intermediate is connected to a radiophore precursor, such as a nitroaryl group $Ar^1$, where $Ar^1$ includes phenyl, naphthyl, and the like, and heteroaryl,

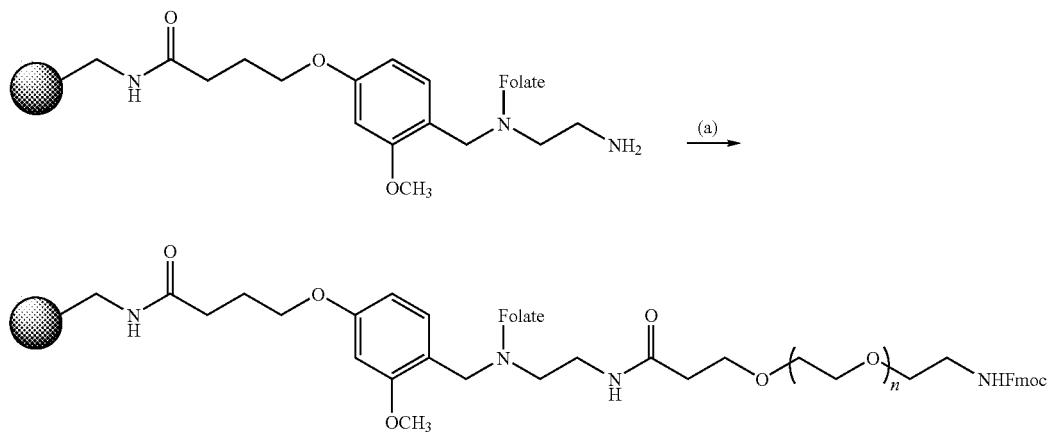

(a) Fmoc-(PEG)$_6$-COOH, HBTU, HOBt, DIPEA, DMF.

such as pyridinyl, piperidinyl, benzoxazole, benzothiazole, and the like, each of which is substituted with at least one nitro group, as shown in the following scheme, where n is an integer from 1 to about 100, from 1 to about 20, or is illustratively in the range from about 3 to about 8:

like. Further, thioamides, ureas, ethers, esters, and other chemical links are described herein for attaching the nitroaryl group.

In another illustrative embodiment of the compounds described herein, where the optional linker is a polyalkylene glycol, a nitroaryl group $Ar^1$ is converted into the corresponding fluoroaryl group $Ar^2$, as shown in the following scheme, where n is an integer from 1 to about 100, from 1 to about 20, or is illustratively in the range from about 3 to about 8:

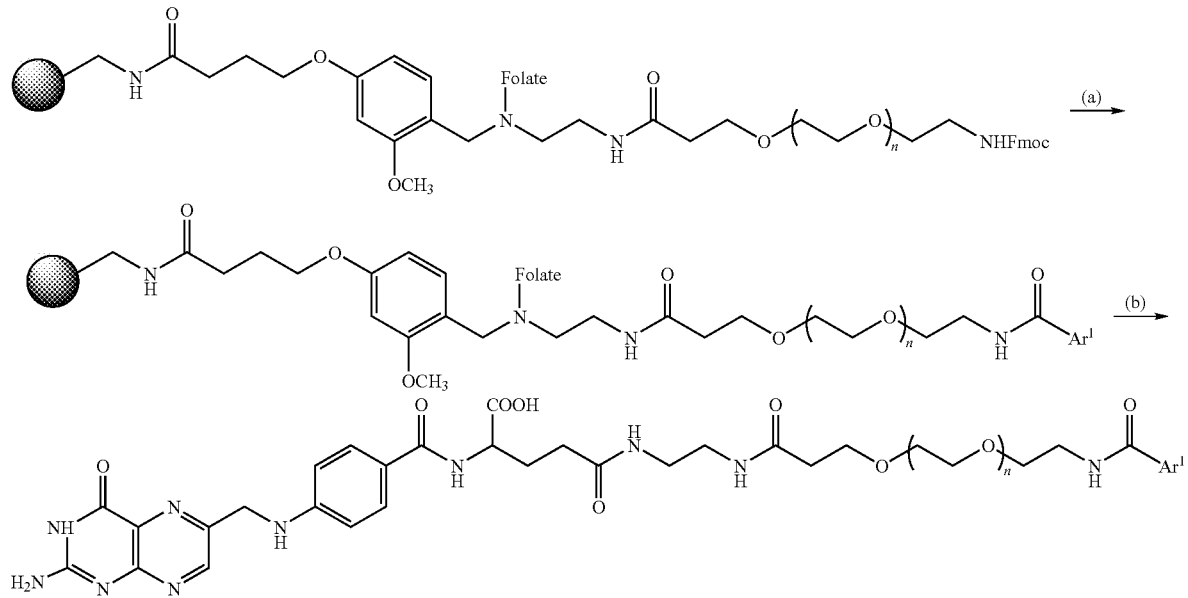

(a) (i) 20% piperidine in DMF, (ii) HOBt, HBTU, DIPEA, DMF, 4-nitrobenzoic acid OR 2,5-dinitrobenzoic acid; (b) (i) 2% NH$_2$NH$_2$ in DMF, (ii) TFA/TIPS/H$_2$O (95:2.5:2.5).

The foregoing scheme is illustrated for nitroaryl containing carboxylic acids;

however, it is to be understood that additional nitroaryl containing compounds, including nitroheteroaryl containing compounds, may be used by the appropriate selection of an attachment atom. For example, reverse amides are described herein, where in the above scheme, the PEG intermediate terminates in a carboxylic acid and the nitroaryl containing group is an aniline, or the corresponding aryl or heteroaryl variation thereof, such as 3-nitro-5-aminopyridine, and the

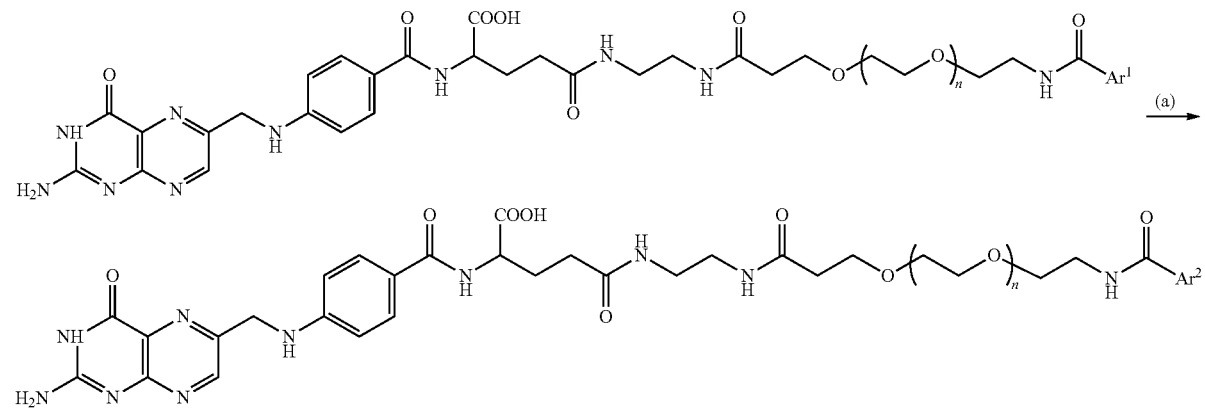

(a) TBA$^{19}$F or TBA$^{18}$F, DMSO; RT, 5-30 min; or K$^{19}$F or K$^{18}$F, 18-Crown-6, DMSO, higher temperature; or TBA$^{19}$F or TBA$^{18}$F, NaHCO$_3$, DMSO, low temperature; or K$^{19}$F or K$^{18}$F, Kryptofix-222, NaHCO$_3$, DMSO, higher temperature.

The foregoing scheme is illustrated for fluoroaryl containing carboxylic acids; however, it is to be understood that additional fluoroaryl containing compounds, including fluoroheteroaryl containing compounds, may be used by the appropriate selection of an attachment atom. For example, reverse amides are described herein, where in the above scheme, the PEG intermediate terminates in a carboxylic acid and the fluoroaryl containing group is an aniline, or the corresponding aryl or heteroaryl variation thereof, such as 3-fluoro-5-aminopyridine, and the like. Further, thioamides, ureas, ethers, esters, and other chemical links are described herein for attaching the fluoroaryl group. It is to be understood that the compounds described herein may include more than one nitro group that may be converted into the corresponding fluoro group. It is also to be understood that the above illustrative syntheses are applicable for preparing both the $^{19}$F and $^{18}$F fluoroaryl compounds, though it is appreciated that the $^{18}$F fluororaryl compounds are adapted for use in the imaging methods described herein using PET.

In another illustrative embodiment, the nitroaryl and the fluoroaryl group is the corresponding phenyl group, as shown in the following scheme where $R^f$ is selected from nitro and fluoro, providing that at least one of $R^f$ is fluoro; m is 1, 2, or 3; and n is an integer from 1 to about 20, and is illustratively 3 or 5:

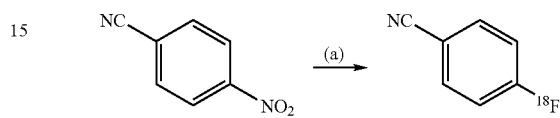

(a) 1.3 eq. anhydrous TBA$^{18}$F, anhydrous DMSO, 30 min; yield > 95%; (b) 1.3 eq. anhydrous TBA$^{18}$F, anhydrous DMSO, < 5 min; yield > 95%.

Additional fluorodenitrofication processes using radioactive conditions such as TBA$^{18}$F/DMSO or K$^{18}$F/DMSO are described herein, as shown in the following scheme.

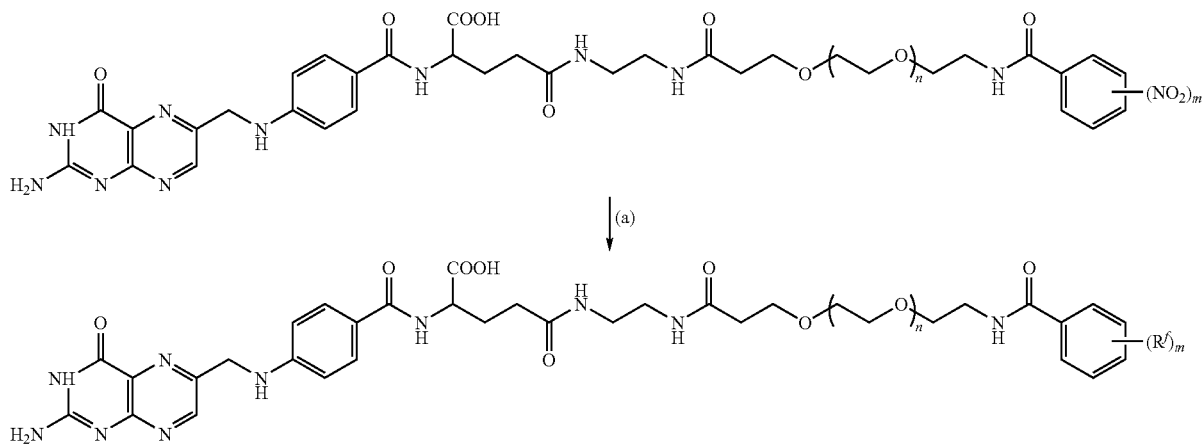

(a) TBA$^{19}$F, DMSO; RT, 5-30 min; OR K$^{18}$F, 18-Crown-6, DMSO, higher temperature; OR (c) TBAF, NaHCO$_3$, DMSO, low temperature; OR KF, Kryptofix-222, NaHCO$_3$, DMSO, higher temperature.

In one aspect, the nitroaryl is 4-nitrophenyl. In another aspect, the nitroaryl is 2,5-dinitrophenyl. In another aspect, the fluoroaryl is 4-fluorophenyl. In another aspect, the fluoroaryl is 5-fluorophenyl. In another aspect, the fluoroaryl is 2,5-difluorophenyl.

It is appreciated that PEG linkers of varying lengths, such as 3, 4, 5, or 6 repeating units may be prepared according to this synthetic procedure. It is also to be understood that the fluorination agent is either an $^{18}$F or a $^{19}$F fluorination reagent, or an isotopic mixture thereof.

Additional fluorodenitrofication processes using radioactive conditions such as TBA$^{18}$F/DMSO or K$^{18}$F/DMSO are described herein, as shown in the following scheme. It is appreciated that these processes may also be adapted to include non-radioisotopes of fluorine, including $^{19}$F, or isotopic mixtures thereof.

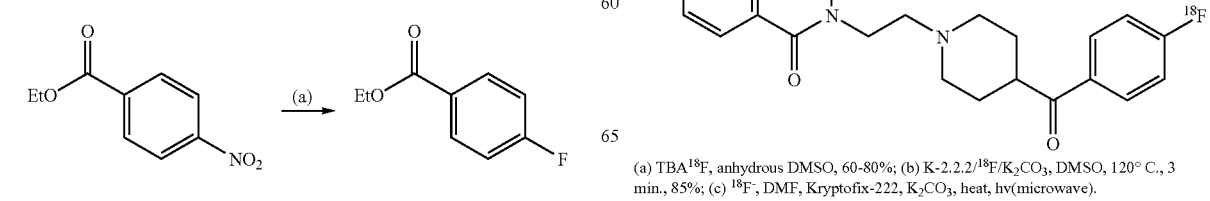

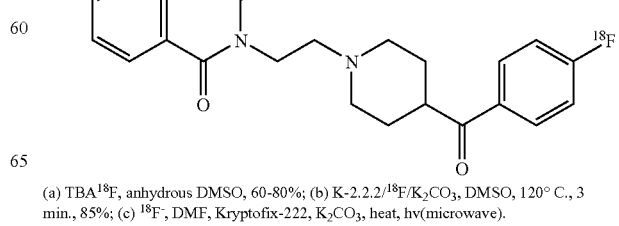

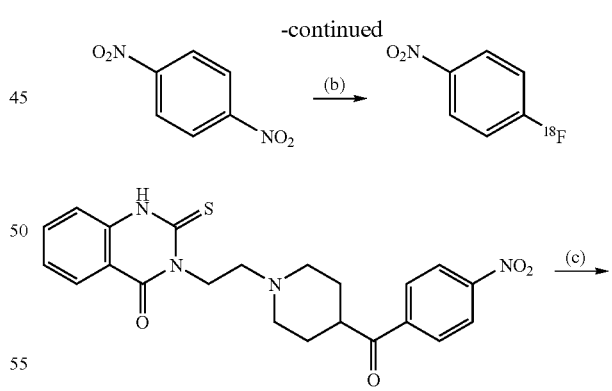

(a) TBA$^{18}$F, anhydrous DMSO, 60-80%; (b) K-2.2.2/$^{18}$F/K$_2$CO$_3$, DMSO, 120° C., 3 min., 85%; (c) $^{18}$F$^-$, DMF, Kryptofix-222, K$_2$CO$_3$, heat, hv(microwave).

Additional synthetic details are described in J. Am. Chem. Soc., 2005, 127, 2050-2051; Angew. Chem. Int. Ed. 2004. 43, 3588-3590; J. Org. Chem. 1984, 49, 3216-3219; J. Am. Chem. Soc. 1974, 96, 2250-2252; J. Chem. Soc, Chem. Commun. 1993, 921-922; J. Fluorine Chem., 1993, 63, 25-30; Applied Radiation and Isotopes 2006, 64, 989-994; Applied Radiation and Isotopes 1999, 50, 923-927; J. Nuc. Med. 1991, 32, 2266-2272; and Angew. Chem. Int. Ed. 2006, 45, 2720-2725, each entirely incorporated herein by reference.

In an alternate process, the radioisotope may be introduced into an intermediate compound rather than the final compound. Illustratively, compounds described herein may be prepared as follows, where LG is a leaving group:

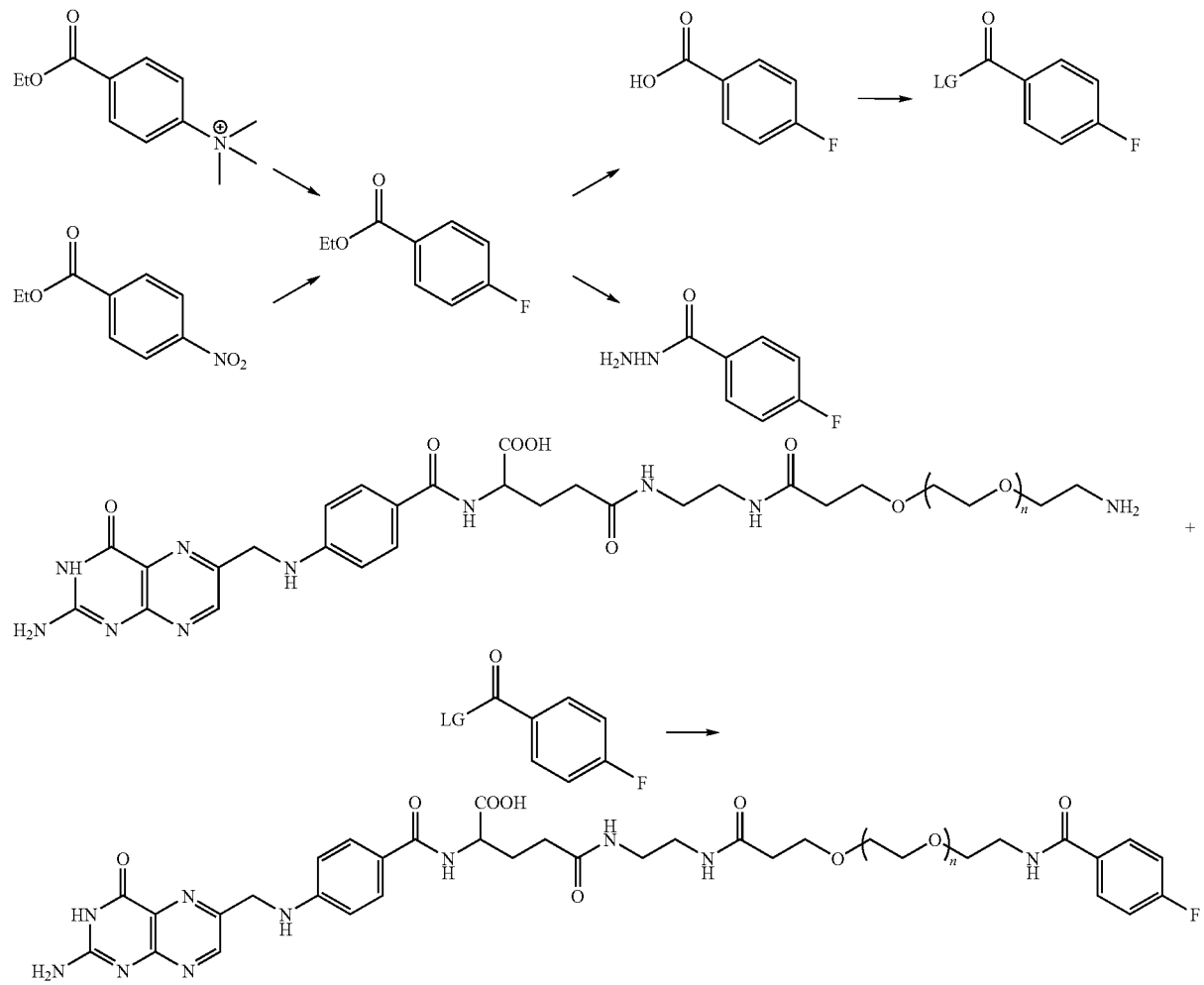

where n is an integer selected from 1 to about 100; in the range from 1 to about 20, or in the range from 3 to about 8. It is understood that either or both of $^{18}F$ and $^{19}F$ isotopes, and mixtures thereof, may be prepared according to the above process.

In an alternate process, the compounds described herein may be prepared as follows:

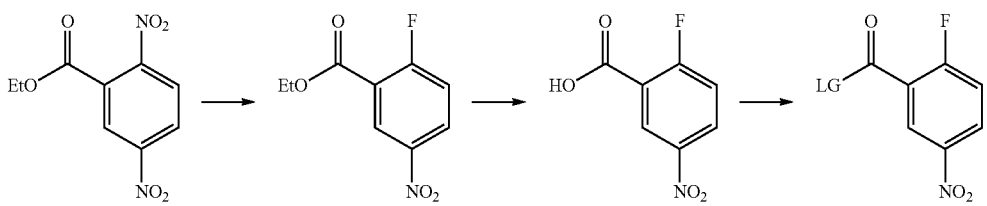

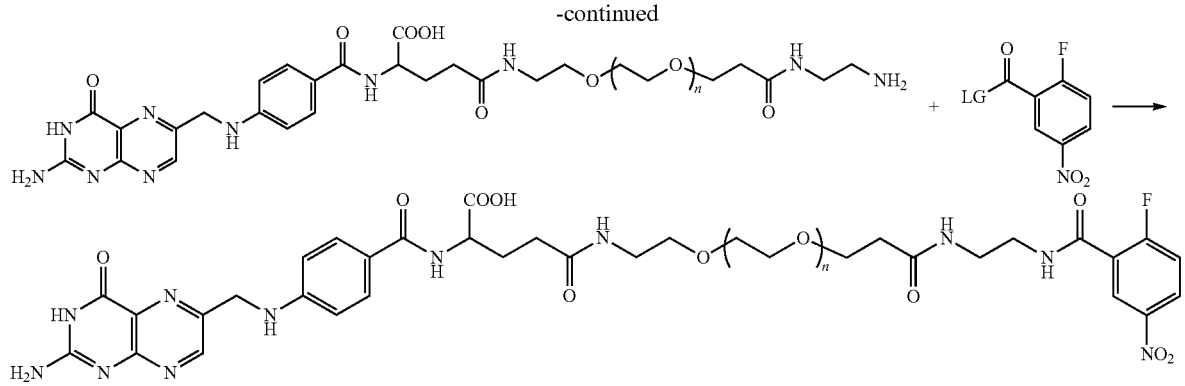

where n is an integer selected from 1 to about 100; in the range from 1 to about 20, or in the range from 3 to about 8. It is understood that either or both of $^{18}F$ and $^{19}F$ isotopes, and mixtures thereof, may be prepared according to the above process.

In an alternate process, the compounds described herein may be prepared as follows:

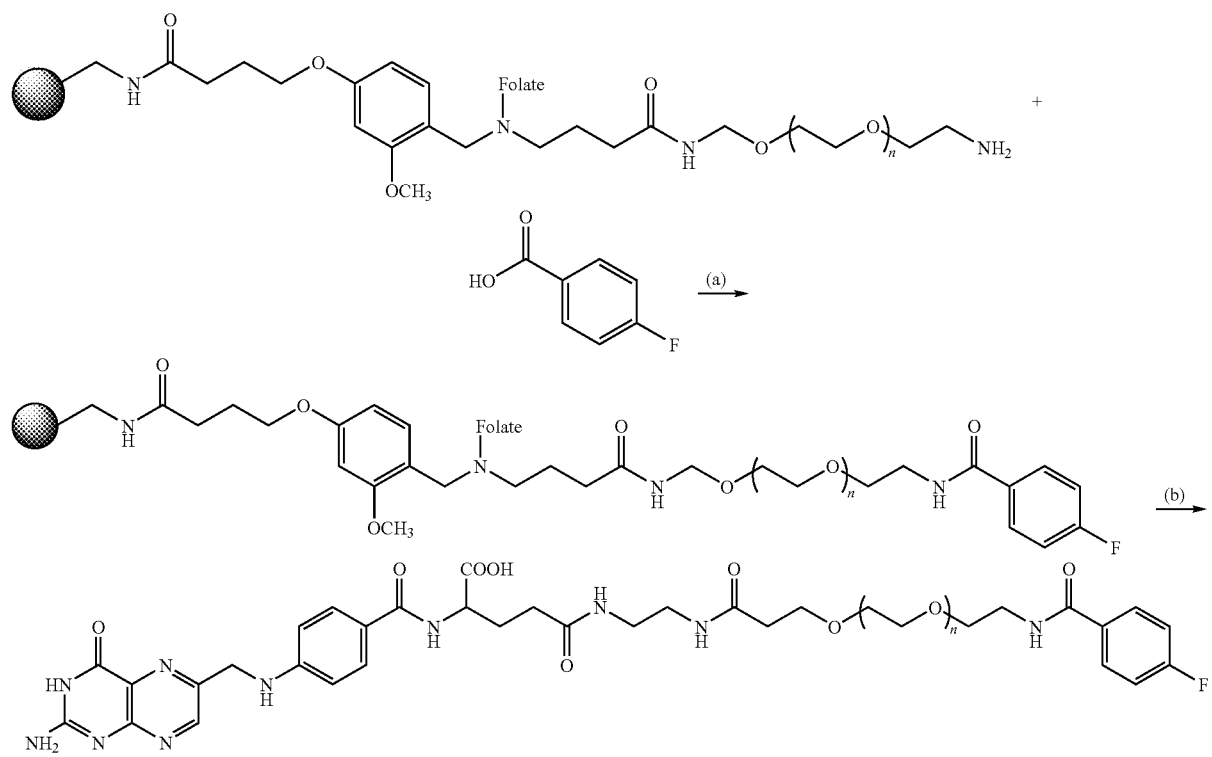

(a) HATU/DIPEA, 3 min., >95%; (b) TFA/phenol/H$_2$O/TIPS 90:4:5:1, 37° C., 10 min. >95% or ambient temperature, 20 min, 65%.

where n is an integer selected from 1 to about 100; in the range from 1 to about 20, or in the range from 3 to about 8. It is understood that either or both of $^{18}F$ and $^{19}F$ isotopes, and mixtures thereof, may be prepared according to the above process. Additional synthetic details are described in Bioorg Med Chem Lett. 10:1501-1503 (2000), entirely incorporated herein by reference.

In an alternate process, the compounds described herein may be prepared as follows:

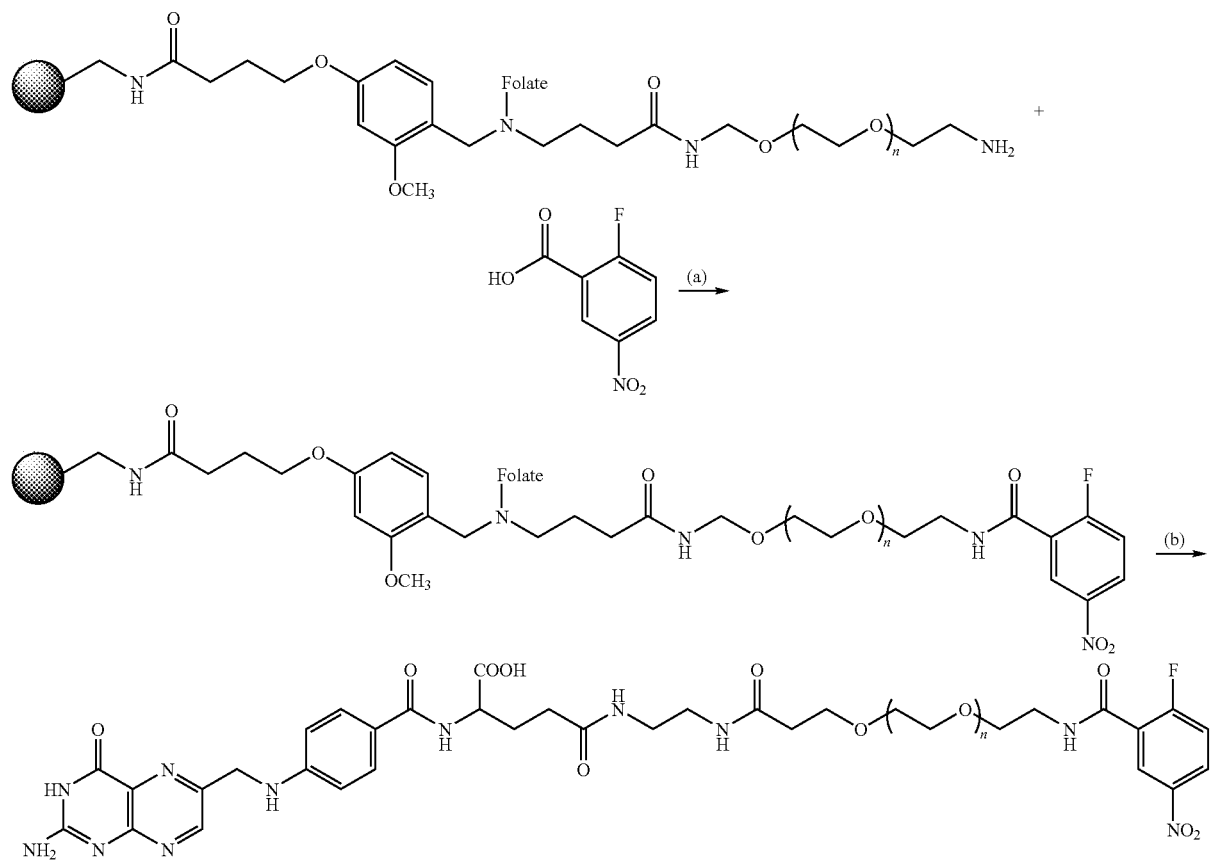

where n is an integer selected from 1 to about 100; in the range from 1 to about 20, or in the range from 3 to about 8. It is understood that either or both of $^{18}F$ and $^{19}F$ isotopes, and mixtures thereof, may be prepared according to the above process.

It is to be understood that the fluorodenitrification step described in the various process embodiments may take place at various steps in the process. However, it is appreciated that conversion late in the synthesis carries the advantage of minimizing the decay time of the radioisotope during imaging agent preparation. However, even when the fluorodenitrification step is performed on an intermediate, the elapsed time complete conversion is as follows: about 3 min for radiolabeling, about 7 min for cleave from the resin, overall time including purification about 25-30 min., radiochemical labeling yield about 70-80%.

The amount of the conjugate effective for use in accordance with the methods described herein depends on many parameters, including the molecular weight of the conjugate, its route of administration, and its tissue distribution.

Illustratively, an "effective amount" of the conjugate is an amount sufficient to bind to cancer cells or activated monocytes or activated macrophages and to be useful in the diagnosis and/or monitoring of cancer or disease states involving activated monocytes or activated macrophages. The effective amount of the conjugate to be administered to a patient being evaluated for cancer or disease states involving activated monocytes or activated macrophages can range from about 1 pg/kg to about 10 mg/kg, 1 ng/kg to about 10 mg/kg, or from about 10 μg/kg to about 1 mg/kg, or from about 100 μg/kg to about 500 μg/kg.

The conjugate can be administered in one or more doses, such as from about 1 to about 3 doses, prior to detection with the extra-corporeal PET imaging device. The number of doses depends on the molecular weight of the conjugate, its route of administration, and its tissue distribution, among other factors. When used for diagnosis and/or monitoring of cancer or disease states involving activated monocytes or activated macrophages, the extra-corporeal detection procedure is typically performed about 1 minute to about 6 hours post-administration of the conjugate, but the extra-corporeal detection procedure can be performed at any time post-administration of the conjugate as long as binding of the conjugate to cancer cells or activated monocytes or activated macrophages is detectable and sufficient time is allowed for elimination of a substantial fraction of the unbound conjugate from the body.

The conjugates administered in accordance with the methods described herein are preferably administered parenterally to the patient, for example, intravenously, intradermally, subcutaneously, intramuscularly, or intraperitoneally, in combination with a pharmaceutically acceptable carrier. Alternatively, the conjugates can be administered to the patient by other medically useful procedures such as in an orally available formulation. It is appreciated that any patient suspected of having cancer or a disease state involving activated monocytes or activated macrophages, whether symptomatic or not, who would benefit from an evaluation using the method of the present invention can be evaluated.

The conjugates used in accordance with the methods are used in one aspect of this invention to formulate diagnostic compositions comprising effective amounts of the conjugate and an acceptable carrier therefor. Examples of parenteral dosage forms include aqueous solutions of the conjugate, for example, a solution in isotonic saline, 5% glucose or other well-known pharmaceutically acceptable liquid carriers such as alcohols, glycols, esters and amides. Any orally available dosage forms known in the art can also be used.

The conjugates use in the methods described herein are formed to target and, thus, to concentrate the conjugate at the site of a tumor or at the site of accumulation of activated monocytes or activated macrophages, such as activated macrophages adhering to the luminal endothelial layer of the plaque or activated macrophages present in the lipid-rich core of the plaque in the patient.

Several aspects of the methods described herein may be advantageous in the detection of cancer cells or activated monocytes or activated macrophages. In one embodiment, the radiophore comprises an elemental isotope which is a positron emitter. Positron emitters emit in three dimensions from the source atom, but the emission proceeds in two parts in exactly opposite directions. As the anti-particle of the electron, when the positron from a decaying isotope comes in contact with electrons in nearby matter, it annihilates emitting energy from the annihilation as gamma rays. To conserve momentum, the gamma ray photons travel in opposite directions. Because the positron has two radiation rays available for detection, the location in the patient where the conjugate has accumulated is more readily and therefore more accurately, detected within a time frame reasonable for patient diagnosis. The signal-to-noise ratio of positron annihilation is markedly improved over unidirectional gamma rays. Further, by back-projecting coincident rays, the location of the source emission is located.

PET is presently used in medical centers as a diagnostic tool for the detection of cancer. In cancer diagnosis, a patient may be administered glucose that has been tagged with a positron emitter, such as $^{18}F$ fluorodeoxyglucose, because glucose concentrates in fast-growing cancer cells. The presence of a cancer may be detected by the concentration of the PET imaging agent. Also, the location of the cancer in the body is determined by back-projecting the coincident gamma radiation by means of the PET scanner. Thus, the methods described herein may be used in combination with $^{18}F$ fluorodeoxyglucose to detect cancer cells. The methods may also be used in combination with any other methods of cancer diagnosis already developed and known in the art, including methods using other already developed diagnostic agents and utilizing x-ray computed tomography (CT), magnetic resonance imaging (MRI), functional magnetic resonance imaging (fMRI), ultrasound, and single photon emission computed tomography (SPECT).

In other embodiments, the methods described herein can be used alone or in combination with any other method(s) known in the art for the detection, analysis, and/or ablation of atherosclerotic plaques. For example, the methods can be used in combination with methods to ablate atherosclerotic plaques in cases where active plaques cause narrowing of blood vessels. In such cases, the conjugates described herein can be used not only to identify active atherosclerotic plaques as compared to inactive plaques, but also to distinguish between atherosclerotic and normal tissue to aid in ablation procedures. Thus, the methods and compositions can be used to analyze both the physiological and the morphological state of atherosclerotic plaques. For example, angioplasty involves the non-surgical widening of a vessel narrowed by plaque deposition, and laser energy, for example, directed through optical fibers in a catheter-based device, can be used to ablate or partially remove the plaque deposits. Catheter-based devices for ablating plaques using laser energy are described in U.S. Pat. Nos. 4,817,601, 4,850,351, and 4,950,266, each entirely incorporated herein by reference.

It is understood that in certain applications of the methods described herein, each of the processes and synthetic methods described herein either substantially complete fluorination, or alternatively only partial fluorination may be desired. Accordingly, the processes and synthetic methods described herein may be performed in various alternative embodiments. It is therefore understood that in those aspects where only partial fluorination is desired, the processes and syntheses described herein may be performed with less than stoichiometric amounts of fluorinating agent. Similarly, it is understood that in certain applications of the methods described herein, each of the processes and synthetic methods described herein either substantially complete radiofluorination, or alternatively only partial radiofluorination may be desired. Accordingly, the processes and synthetic methods described herein may be performed in various alternative embodiments. It is therefore understood that in those aspects where only partial radiofluorination is desired, the processes and syntheses described herein may be performed with less than stoichiometric amounts of radiofluorination agent, where the balance is optionally $^{19}F$.

It is further understood that in certain applications of the methods described herein, each of the processes and synthetic methods described herein wherein there is present more than one nitro group, reactions may selected in various alternative embodiments. In one alternative, stoichiometric amounts of the fluorination agent are included to substantially convert each nitro group into the corresponding fluoro group. In another alternative, the amount of fluorination agent is selected to substantially convert only a subset of nitro groups, such as one or two nitro groups out of three that may be present; or in one variation, one nitro group out of two that may be present. In another variation, less than one equivalent of fluorinating agent is included in the process to only partially convert at least one nitro group to the corresponding fluoro group. It is appreciated that the various embodiments are selected to suit the intensity of labeling needs for the methods described herein. It is appreciated that in those aspects where substantial conversion of all intro groups present will not take place, the presence of additional nitro groups may act as activating groups to decrease the reaction time or to increase the overall conversion to the desired partial level of fluorination. Accordingly, also contemplated herein are compounds that may include additional electron withdrawing groups, or alternative electron withdrawing groups other than nitro that we either decrease the reaction time or to increase the overall conversion to the desired partial level of fluorination.

The following examples are described and intended to further illustrate selected embodiments of the invention described herein. The following examples should not be construed as limiting the invention in any way.

EXAMPLES $^{18}F$ N-Hydroxysuccinimde 4-Fluorobenzoate

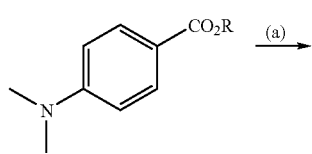

-continued

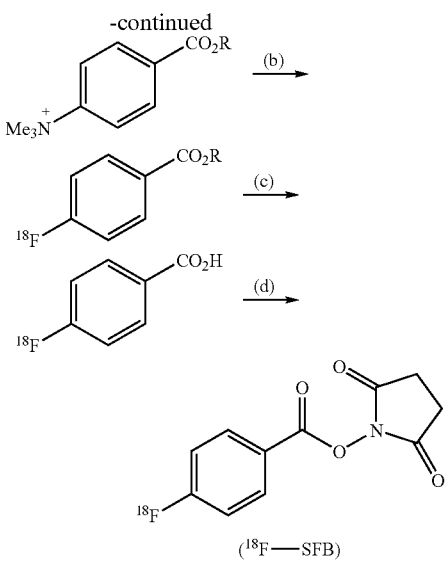

($^{18}$F—SFB)

(a) methyl triflate; (b) $^{18}$F/K$_2$CO$_3$/Kryptofix (K2.2.2, Aldrich Catalog number 29,111-0), dimethyl sulfoxide (DMSO), 90° C., 10 min.; (c) NaOH, 90° C., 5 min.; (d) N-Hydroxysuccinimide tetramethylurea (TSTU), CH$_3$CN, 120° C., 5 min.

The p-fluorobenzoic acid may be purified and concentrated by the addition of sufficient HCl to fully protonate the p-fluorobenzoic acid, which are isolated on a reverse phase C18 column such as a C18 SepPak Plus sold by Waters Corp. Milford Massachusetts. The column may be washed with HCl acidified water to remove any water soluble contaminants. The p-fluorobenzoic acid may be eluted from the column with methanol followed by further contaminant removal on a cationic ion-exchange column (e.g., a Dowex column), and concentration by evaporation of the methanol. It is to be understood that the foregoing synthesis is also used to make isotopic mixtures that include $^{18}$F and $^{19}$F.

The N-hydroxysuccinimide ester of p-fluorobenzoic acid may be concentrated and purified after isolation by reverse phase high performance liquid chromatography in a mixture of water/acetonitrile/and sufficient trifluoroacetic acid to preserve an acidic pH. A water diluted solution of the ester may be concentrated on a C18 SepPak column followed by elution with diethyl ether. Residual water may be removed using a column of anhydrous Mg$_2$SO$_4$. After evaporation of the ether to dryness, the ester may be re-dissolved in CH$_3$CN.

An alternate synthesis of $^{18}$F-SFB was performed using a procedure modified from that described in Eur. J. Med. Mol. Imaging, vol. 31: 469-474 (2004), entirely incorporated herein by reference. Starting from $^{18}$F-fluorobenzoic acid, prepared as described in processes described herein, an oil bath was set up at 90° C. A solution was made of 45% tetramethlyammonium hydroxide (TMAH) in water. In a separate vial, 10.0 mg of 4-fluorobenzoic acid was added (solution 1). In a separate vial, 40 µl of 45% TMAH was added (solution 2). Then 0.2 ml of water and 1.0 ml of acetonitrile was added and solution 2 was added to solution 1 (solution 3). The solution was evaporated to dryness. In another vial, 14 mg of TSTU was added to 1.2 ml acetonitrile (solution 4). Solution 4 was added to solution 3. The mixture was heated to 90 degrees Celsius in an oil bath for 2 minutes. Radioactive $^{18}$F will be synthesized in a cyclotron by procedures well-known in the art and used to prepare ($^{18}$F)-para-fluorobenzoic acid, as shown in Example 1, which will then be converted to $^{18}$F-SFB as described above.

It is appreciated that the foregoing processes may be used with other aromatic carboxylic acids having a dimethylamine group to prepare the corresponding $^{18}$F labeled radiophore for conjugation as described herein. In addition, it is to be understood that in the foregoing illustrative process, the intermediate ($^{18}$F)SFB may be coupled to any other folic acid, or analog or derivative thereof, through an optional linker as described herein to form a conjugate. It is further appreciated that the aryl ring may be optionally substituted.

N(10)-TFA Pteroic Acid. The synthesis was performed as described in WO 2006/009153. Briefly, zinc chloride was added to a solution of folic acid dissolved in 0.1M tris base. Carboxypeptidase G was added to the reaction while stirring. The pH was adjusted to about 7.3 using 1N HCl and temperature was raised to 30° C. The reaction vessel was covered with aluminum foil and stirred for 7 days. The pH was adjusted as needed to about 7.3. The pH was lowered to about pH 3.0 using 6N HCl. The resulting precipitate was centrifuged at 4000 rpm for 10 min. The supernatant was decanted and lyophilized for 48 h. Pteroic acid was purified using ion exchange column, and the fractions lyophilized for 48 h. The pteroic acid was dried under vacuum for 24 h and then kept under argon for 30 min. Trifluoroacetic anhydride was added and stirred at room temperature under argon for 4 days (the reaction vessel was wrapped with aluminum foil). Progression of the reaction was monitored by analytical HPLC (Waters, X-Bridge C18; 3.0×50 mm, 1% B to 50% B in 30 min, 80% B wash 35 min run) until a single peak was observed (λ=280 nm, 320 nm). The solvent was evaporated and 3% TFA in water was added followed by stirring for two days. After centrifuging at 3000 rpm for 20 min, the solvent was decanted and solid was washed with water, and centrifuged three times. The TFA protected pteroic acid was lyophilized for 48 h.

Universal Folate Resin. Universal Folate resin was synthesized using Universal NovaTag™ resin (Novabiochem; Catalog #04-12-3910), as described in Novabiochem Letters 1-4 (2004); Bioorg. Med. Chem. Left. 15:5442-5445 (2005), the disclosures of which are incorporated herein by reference. After swelling the resin with dichloromethane (DCM), and then with DMF, the Fmoc was removed with 20% piperidine in DMF. The resulting Fmoc-Glu-OtBu was coupled using HATU [2-(1H-7-Azabenzotriazol-1-yl)-1,1,3,3-tetramethyl uronium hexafluorophosphate] and DIPEA (N,N-Diisopropylethylamine) in DMF. Similarly, N10-TFA Pteroic was coupled using standard Fmoc solid phase peptide synthesis (SPPS). The pendant Mmt (4-Methoxytrityl) was removed with 1M HOBt (1-Hydroxybenzotriazole) in DCM/trifluoroethanol. The resin may be washed with DMF and immediately used again, or it may be washed with DCM/DMF and then with MeOH and dried for later use.

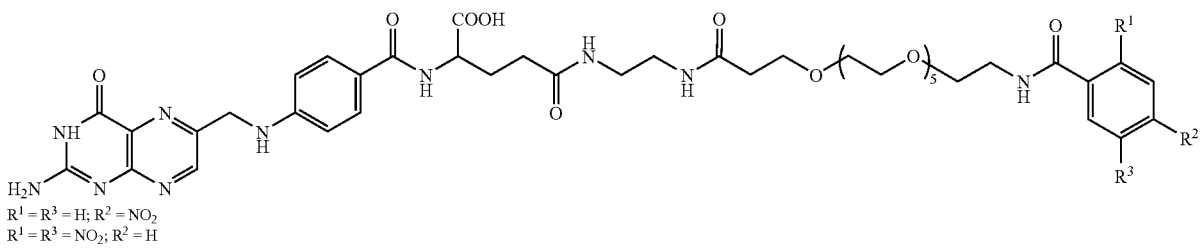

$R^1 = R^3 = H; R^2 = NO_2$
$R^1 = R^3 = NO_2; R^2 = H$

Folate PEG Conjugates of Radiophore Precursors. Fmoc-(PEG)$_6$-CO$_2$H was coupled to Universal folate resin using HOBt/HBTU (O-Benzotriazole-N,N,N',N'-tetramethyl-uronium-hexafluoro-phosphate)/DIPEA in DMF. The Fmoc group was removed using 20% piperidine and then either 4-nitrobenzoic acid or 2,5-dinitrobenzoic acid was introduced using HOBt/HBTU/DIPEA in DMF. A hydrazine solutions (2%) was used to deprotect the N10-TFA group, followed by treatment with TFA/triisopropylsilane/water to cleave the compound from the resin and deprotect the tertiary butyl groups. The solvent was concentrated under vacuum and the compounds were precipitated using diethyl ether.

Both folate-nitro-phenyl conjugates were purified using reverse phase preparative HPLC (Waters, NovaPak C18; 19×300 mm) A=10 mM NH$_4$OAc (pH=7.0), B=Acetonitrile; λ=320 nm; solvent gradient: 1% B to 50% B in 25 min, 80% B wash 40 min run. Purified compounds were analyzed using reverse phase analytical HPLC (Waters, X-Bridge C18; 3.0× 50 mm) giving a single peak at λ=280 nm, 320 nm; 1% B to 50% B in 10 min, 80% B wash 15 min run.

Folate-4-nitrophenyl conjugate: yellow solid, R$_t$~8.58 min (analytical HPLC); ESI-MS (M+H)$^+$=968; ESI-MS (M−H)$^−$=966; $^1$H NMR (Bruker 500 MHz cryoprobe, DMSO-d$_6$/D$_2$O, to remove exchangeable protons) δ 1.88 (m, 1H, Glu-H); 2.03 (m, 1H, Glu-H); 2.15 (t, J=7.4, 2H, Glu-H); 2.28 (t, J=6.4, 2H, Linker-H); 3.05 (m, 4H, Linker-H); 3.20-3.60 (Linker-H); 4.23 (m, 1H, Glu-αH); 4.48 (s, 2H, Ptc-H); 6.64 (d, J=8.8 Hz, 2H, Ptc-Ar—H); 7.64 (d, J=8.8 Hz, 2H, Ptc-Ar—H); 8.08 (d, J=8.8, 2H, Ar—H); 8.31 (d, J=8.8, 2H, Ar—H); 8.63 (s, 1H, Ptc-Ar—H).

Folate-2,5-dinitrophenyl conjugate: yellow solid, R$_t$~8.4 min (analytical HPLC); ESI-MS=1013 (M+H)+; 1011 (M−H)−; 1H NMR (Bruker 500 MHz cryoprobe, DMSO-d$_6$/D$_2$O, to remove exchangeable protons) δ 1.88 (m, 1H, Glu-H); 2.03 (m, 1H, Glu-H); 2.15 (t, J=7.4, 2H, Glu-H); 2.28 (t, J=6.4, 2H, Linker-H); 3.05 (m, 4H, Linker-H); 3.20-3.60 (Linker-H); 4.23 (m, 1H, Glu-αH); 4.48 (s, 2H, Ptc-H); 6.64 (d, J=8.8 Hz, 2H, Ptc-Ar—H); 7.64 (d, J=8.8 Hz, 2H, Ptc-Ar—H); 8.34 (d, J=8.6, 1H, Ar—H); 8.54 (d, J=8.6, 1H, Ar—H); 8.63 (s,1H, Ptc-Ar—H); 8.90 (s, 1H, Ar—H).

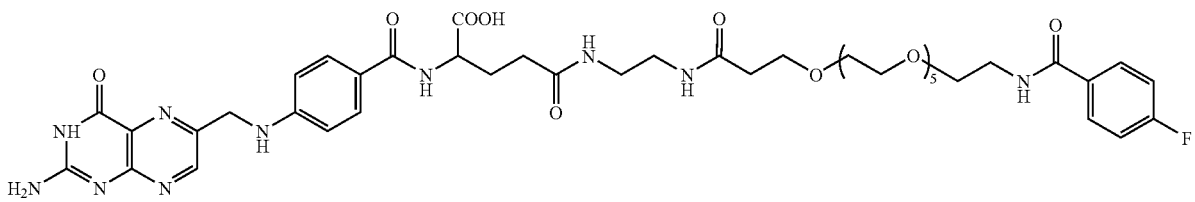

Folate Fluoro Radiophore Conjugates. The folate-nitrophenyl conjugates were dried under vacuum using P$_2$O$_5$ over 24 hours. Dried folate nitro conjugates were dissolved in DMSO-d$_6$. Anhydrous TBAF (tetrabutylammonium fluoride) was added to convert the folate-fluoro-phenyl conjugates. The progress of the reaction was monitored by $^1$H-NMR. Both folate-fluorophenyl conjugates were purified using reverse phase preparative HPLC (Waters, NovaPak C18 ; 19×300 mm) A=10 mM NH4OAc (pH=7.0), B=Acetonitrile; λ=320 nm; Solvent gradient: 1% B to 50% B in 25 min, 80% B wash 40 min run. Purified compounds were analyzed using reverse phase analytical HPLC (Waters, X-Bridge C18; 3.0× 50 mm) and they gave a single peak at λ=280 nm, 320 nm; 1% B to 50% B in 10 min, 80% B wash 15 min run. Additional synthetic details are described in Angew. Chem. Int. Ed. 45:2720-2725 (2006), the disclosure of which is incorporated herein by reference.

Folate-4-fluorophenyl conjugate: yellow solid, R$_t$~8.46 min (analytical HPLC); ESI-MS (M+H)$^+$=941; ESI-MS (−H)$^−$=939; $^1$H NMR (Bruker 500 MHz cryoprobe, DMSO-d$_6$/D$_2$O, to remove exchangeable protons) δ 1.88 (m, 1H, Glu-H); 2.03 (m, 1H, Glu-H); 2.15 (t, J=7.4, 2H, Glu-H); 2.28 (t, J=6.4, 2H, Linker-H); 3.05 (m, 4H, Linker-H); 3.20-3.60 (Linker-H); 4.23 (m, 1H, Glu-αH); 4.48 (s, 2H, Ptc-H); 6.64 (d, J=8.8 Hz, 2H, Ptc-Ar—H); 7.28 (t, J=8.9 Hz, 2H, Ar—H); 7.64 (d, J=8.8 Hz, 2H, Ptc-Ar—H); 7.90 (t, J=8.9 Hz, 2H, Ar—H); 8.63 (s,1H, Ptc-Ar—H).

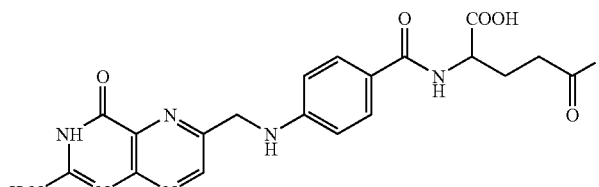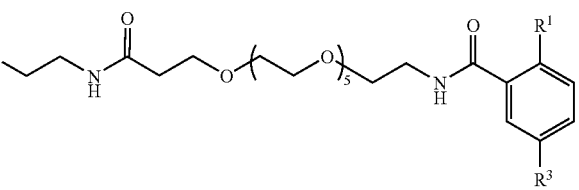

$R^1 = F, R^3 = NO_2$
$R^1 = NO_2, R^3 = F$
$R^1 = R^3 = F$

The above procedure was followed to prepare additional fluorophenyl cohjugates. It is to be understood that the 19F and 18F analogs are prepared in an analogous fashion by selecting the appropriate isotopic reagent. Illustratively, the $^{18}$F compounds described herein are prepared using TBAF$^{18}$F in DMSO at ambient temperature for 10-20 minutes, or [K/2.2.2]$^{18}$F/K$_2$CO$_3$ in DMSO at elevated temperature, as described in Bioconjugate Chem. 2:44-49 (1991); Applied Radiation and Isotopes 64:989-994 (2006); J Label Compd Radiopharm 49:1037-1050 (2006); Applied Radiation and Isotopes 50:923-927 (1999); J. Nuc. Med. 32:2266-2272 (1991).

Analysis by HPLC. Impure and purified samples of folate conjugates of SFB, and other radiophores may be analyzed by high performance liquid chromatography (HPLC) using conditions similar to those described in *Clinical Science*, vol. 103: pp. 4S-8S (2002) with the following modifications. The reverse phase HPLC was performed using a C18 column and the following gradient water/0.1% TFA in CH$_3$CN at 77:23 for 10 min, 60:40 for 10 min, 50:50 for 10 min, 40:60 for 10 min, and using a flow rate of 1.0 ml/minute.

Analysis by ESI-MS. Impure and purified samples of folate conjugates of SFB, and other radiophores may be analyzed by ESI-mass spectrometry.

Competitive binding assay using KB cells. Relative binding affinity of the folate-fluoro-phenyl conjugate was evaluated according to the standard literature protocol by Westerhof et. al. (Mol Pharmacol, 1995, 48, 459-471) and C. P. Leamon et. al. (Bioconjugate Chem., 2006,17 (5), 1226-1232) with minor modification. Relative affinity is defined as the inverse molar ratio of compound required to displace 50% of 3H-folic acid bound to folate receptor (FR) on cells, relative affinity of folic acid=1. Therefore, a relative affinity of the comparative ligand=1 suggests a ligand with equal affinity for FR when compared to folic acid; Relative affinity<1 suggests weaker affinity, and a relative affinity>1 suggest a stronger affinity with respect to folic acid.

KB cells (human cervical cancer cell line that shows over expressed FR) were seeded in 48 well falcon plate and allowed to grow adherent monolayer overnight in folate deficient RPMI (Gibco RPMI medium 1640, catalog #27016) that has 10% FBS (Fatal Bovine serum) and 1% PS (penicillin streptomycine). Then cells were incubated with 10 nM 3H-folic acid in the presence of increasing concentration (0.1 nM-1 µM) of cold folic acid (non-radioactive) or folate-fluoro-phenyl conjugate at 37° C. for 1 h. Then cells were rinsed three times with 250 µL of PBS (phosphate saline buffer) and one time with trichloro-acetic acid. 1% sodium dodecylsulfate (250 µL) in PBS were added to each well and after 10 min cell lysates were transferred to individual vials containing 3 mL of scintillation cocktail and radioactivity was counted. From the plot of bound radio activity verses concentration of unlabeled folate-nitro-phenyl conjugate was used to calculate the IC$_{50}$ value (concentration of ligand required to block 50% of 3H-folic acid binding). Results shows folate-4-F-phenyl conjugate has equal or higher affinity for FR when compared to folic acid. Having six polyethylene glycol units makes folate-4-F-phenyl conjugates more water soluble when compare to folic acid, so this may be pne of the reason to higher affinity for FR.

Serum binding assay was carried out according to the stranded protocol that followed by Endocyte. Briefly, 1 mM folate-fluoro-phenyl conjugate in PBS (pH=7.4) was prepared. Then 190 µL of human serum was added to three separate micro-centrifuge tubes (microcon YM-30 NMWL centrifuge filters 0.5 mL) and 190 µL of PBS (pH=7.4) was added another micro-centrifuge tube. Then 10 µL of 1 mM folate-fluoro-phenyl conjugate was added to each tube to give final volume of 200 µL. Also, 190 µL of human serum plus 10 µL of PBS was added to separate micro-centrifuge tubes as blank test. Al samples were transferred into separate micron 30 spin filters and centrifuged at 10,000×g for 30 min at room temperature. Recovered filtrates were analyzed by analytical HPLC (Waters, X-Bridge C18; 3.0×50 mm, and they gave a single peak at λ=280 nm, 320 nm; 1% B to 50% B in 10 min, 80% B wash 15 min run) and % serum binding was calculated. Since folate-4-F-phenyl conjugate has lower percent serum biding (12.2%), this compound may have lower liver and kidney uptake.

What is claimed is:

1. A compound of the formula

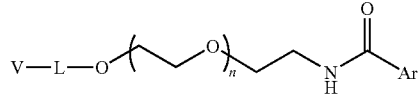

wherein V is a folate receptor binding moiety, or an analog thereof; L is an optional bivalent linker; n is an integer selected from 1 to about 5; and Ar is an aryl group, that includes one or more substituents $(R^f)_m$ comprising a radiophore or a precursor to a radiophore, where m is an integer selected from 1 to about 3.

2. The compound of claim 1 of the formula

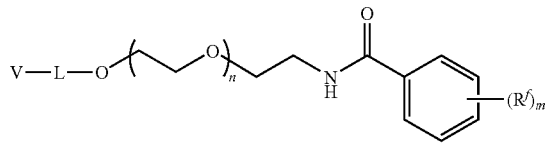

wherein V is a folate receptor binding moiety, or an analog thereof; L is an optional bivalent linker; n is an integer selected from 1 to about 5; $R^f$ comprises a radiophore or a precursor to a radiophore; and m is an integer selected from 1 to about 3.

3. The compound of claim 1 wherein the folate receptor binding moiety is folic acid or a folic acid analog.

4. The compound of claim 1 of the formula

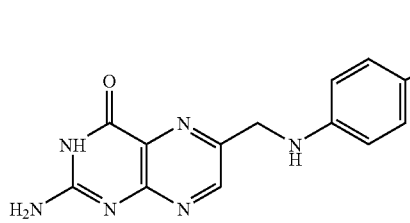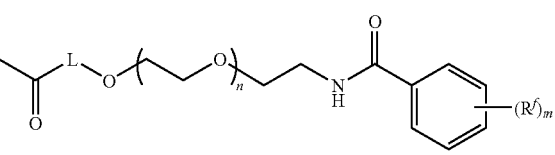

wherein L is an optional bivalent linker; n is an integer selected from 1 to about 5; $R^f$ comprises a radiophore or a precursor to a radiophore; and m is an integer selected from 1 to about 3.

5. The compound of claim 1 wherein m is 1 or 2.

6. The compound of claim 1 wherein $R^f$ comprises one or two nitro groups.

7. The compound of claim 1 wherein $R^f$ comprises one or two $^{18}$F fluoro groups.

8. The compound of claim 1 wherein $R^f$ comprises at least one nitro group and at least one $^{18}$F fluoro group.

9. The compound of claim 1 wherein the L is a linker comprising a plurality of hydrophilic groups.

10. The compound of claim 9 wherein the plurality of hydrophilic groups are independently selected carbohydrates, or analogs-thereof.

11. The compound of claim 1 wherein L is a linker comprising one or more groups that retard reticuloendothelial system uptake of the conjugate.

12. The compound of claim 1 wherein L is a linker comprising one or more groups that retard liver uptake of the conjugate.

13. A composition comprising a compound of claim 1, and a carrier therefor, where the compound is present in an amount sufficient for use in positron emission tomography.

* * * * *